United States Patent
Hong et al.

(10) Patent No.: US 12,377,026 B2
(45) Date of Patent: Aug. 5, 2025

(54) DENTAL ADHESIVE MATERIAL KIT

(71) Applicant: KURARAY NORITAKE DENTAL INC., Kurashiki (JP)

(72) Inventors: Ling Hong, Tokyo (JP); Nobusuke Kashiki, Aichi (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 976 days.

(21) Appl. No.: 17/297,768

(22) PCT Filed: Nov. 27, 2019

(86) PCT No.: PCT/JP2019/046426
§ 371 (c)(1),
(2) Date: May 27, 2021

(87) PCT Pub. No.: WO2020/111142
PCT Pub. Date: Jun. 4, 2020

(65) Prior Publication Data
US 2021/0393488 A1 Dec. 23, 2021

(30) Foreign Application Priority Data
Nov. 28, 2018 (JP) ................................. 2018-222353

(51) Int. Cl.
*A61K 6/30* (2020.01)
*A61K 6/60* (2020.01)
*A61K 6/79* (2020.01)

(52) U.S. Cl.
CPC .................. *A61K 6/30* (2020.01); *A61K 6/60* (2020.01); *A61K 6/79* (2020.01)

(58) Field of Classification Search
CPC ... A61K 6/30; A61K 6/60; A61K 6/79; A61K 6/61; A61K 6/887; C08L 33/10; C08K 33/10
See application file for complete search history.

(56) References Cited

U.S. PATENT DOCUMENTS 9,889,070 B2 * 2/2018 Kashiki ................ C08F 22/38
10,478,385 B2 * 11/2019 Suzuki .................... A61K 6/84
(Continued)

FOREIGN PATENT DOCUMENTS

JP     2007-56020 A    3/2007
JP     2012-162490 A    8/2012
(Continued)

OTHER PUBLICATIONS

Extended European Search Report issued Jul. 21, 2022 in European Patent Application No. 19890357.7, 46 pages.
(Continued)

*Primary Examiner* — Sanza L. McClendon
(74) *Attorney, Agent, or Firm* — Oblon, McClelland, Maier & Neustadt, L.L.P.

(57) ABSTRACT

A dental adhesive material kit may have desirable adhesive properties for tooth structure, and, while ensuring appropriate strength, may allow easy removal of excess cement in a semi-cured state created by temporarily applying light to excess portions of cement with a photoirradiator. Such a dental adhesive material kit may include a dental aqueous adhesive composition (A) and a dental curable composition (B), satisfying the inequality (I)

$$0 \leq t2 - t1 \leq 3.0 \quad (I),$$

wherein t1 (min) is a contactual polymerization start time of the dental aqueous adhesive composition (A) and the dental curable composition (B), and t2 (min) is a polymerization start time of the dental curable composition (B).

20 Claims, 3 Drawing Sheets

(56) References Cited

U.S. PATENT DOCUMENTS

| | | |
|---|---|---|
| 2007/0040151 A1 | 2/2007 | Utterodt et al. |
| 2010/0130682 A1 | 5/2010 | Hinamoto et al. |
| 2010/0267856 A1 | 10/2010 | Shinoda et al. |
| 2016/0051450 A1 | 2/2016 | Kashiki et al. |

FOREIGN PATENT DOCUMENTS

| | | | |
|---|---|---|---|
| JP | 2018-95575 A | 6/2018 | |
| WO | WO 2008/087977 A1 | 7/2008 | |
| WO | WO-2013046648 A1 * | 4/2013 | ................ C08F 4/40 |
| WO | WO-2014156077 A1 * | 10/2014 | ........... A61K 6/0047 |

OTHER PUBLICATIONS

Office Action obtained Aug. 8, 2023, in corresponding Japanese Patent Application No. 2020-557790 (with English Translation), 10 pages.

Communication pursuant to Rule 114(2) EPC issued Aug. 7, 2023, in corresponding European Patent Application No. 19890357.7, 12 pages.

Catalog of "G-CEM ONE" 2017(GC Corporation) (with its partial translation), 5 pages.

Attached document of G-CEM ONE (with its partial translation), 4 pages.

Third party observations obtained Aug. 8, 2023, in corresponding Japanese Patent Application No. 2020-557790 (with English Translation), 10 pages.

Third party observations issued Aug. 7, 2023, in corresponding European Patent Application No. 19890357.7, 12 pages.

International Search Report issued on Feb. 25, 2020 in PCT/JP2019/046426 filed on Nov. 27, 2019, 2 pages.

Third Party Observations issued Oct. 17. 2023, (client obtained on Nov. 7, 2023) in corresponding Japanese Patent Application No. 2020-557790 (with English Translation), 20 pages.

Notice of Submission of Publications issued Aug. 29, 2024 in Japanese Patent Application No. 2020-557790 (with unedited computer-generated English translation), 12 pages.

Notice of Submission of Publications dated Oct. 29, 2024, (client obtained on Nov. 26, 2024) in corresponding Japanese Patent Application No. 2020-557790 (with English Translation), 12 pages.

* cited by examiner

DENTAL ADHESIVE MATERIAL KIT

CROSS-REFERENCE TO RELATED APPLICATIONS

The present application is the national stage of international application PCT/JP2019/046426, filed on Nov. 27, 2019, and claims the benefit of the filing date of Japanese Appl. No. 2018-222353, filed on Nov. 28, 2018.

TECHNICAL FIELD

The present invention relates to a dental adhesive material kit that includes a dental aqueous adhesive composition and a dental curable composition, particularly, a dental adhesive material kit best suited as a dental cement kit.

BACKGROUND ART

A dental cement is a material used to lute a prosthesis, such as a crown, an inlay, or a bridge, to defective areas of teeth.

The material of prosthesis is typically metal or ceramic, and dental cements usually have high adhesive properties for these materials. However, the adhesive properties for tooth structure are generally weak. Another issue is that, because a polymerization initiator is uniformly dispersed in a dental cement, radicals occur in a uniform fashion, and create a contraction force toward the center of the dental cement when the cement is cured alone. This contraction force acts to detach the dental cement from tooth structure, and decreases the adhesive properties.

As a countermeasure, a dental cement kit combining a primer and a dental cement is in common use. The primer used for such a dental cement kit penetrates the tooth structure, and provides increased adhesive properties for tooth structure. In curing the primer and the dental cement, more radicals occur at the primed tooth surface, and the extent of polymerization and cure is greater at the tooth surface. Here, the resulting contraction force in the dental cement acts toward the tooth surface, and the adhesive properties do not decrease. In this way, a common dental cement kit can achieve high adhesive properties for both tooth structure and prosthesis.

Patent Literature 1 proposes a dental composition containing a hydroperoxide compound having one or more hydroperoxide groups attached to tertiary carbons; a thiourea derivative; and a soluble copper compound.

Patent Literature 2 discloses an adhesive kit comprising a curable composition and a pretreatment agent, where the curable composition contains a hydroperoxide compound, a substituted ethylene thiourea compound having a specific structure with a substituent introduced to a cyclic structure moiety, and a vanadium compound and/or a copper compound, and the pretreatment agent contains an acidic group-containing radical polymerizable monomer, a polymerization accelerator, a solvent, and a hydrophilic radical polymerizable monomer having no acidic group.

CITATION LIST

Patent Literature

Patent Literature 1: JP 2007-56020 A
Patent Literature 2: WO2014/156077

SUMMARY OF INVENTION

Technical Problem

However, studies by the present inventors revealed that, when the combination of a hydroperoxide compound, a thiourea derivative, and a soluble copper compound disclosed in Patent Literature 1 is applied to a dental composition, the dental composition does not form a strong adhesive layer upon contact with a primer because of insufficient curing toward the tooth surface, and fails to provide high bond durability for tooth structure. In the adhesive kit described in Patent Literature 2, the dental cement polymerizes to different extents in portions contacting the primer and in portions not in contact with the primer, and further improvements are needed for removal of excess cement by photoirradiation.

It is accordingly an object of the present invention to provide a dental adhesive material kit having desirable adhesive properties for tooth structure, and that, while ensuring appropriate strength, enables easy removal of a marginal excess cement in a semi-cured state created by temporarily applying light to excess portions of cement with a photoirradiator in bonding a crown restoration to tooth structure.

Solution to Problem

The present inventors conducted intensive studies to overcome the technical issues stated above, and found that the foregoing issues can be solved by setting a specific range for a relationship between a contactual polymerization start time of a dental aqueous adhesive composition and a dental curable composition, and a polymerization start time of a dental curable composition. The present invention was completed on the basis of this finding.

Specifically, the present invention provides the following.
(1) A dental adhesive material kit comprising a dental aqueous adhesive composition (A) and a dental curable composition (B), and satisfying the following formula (I)

$$0 \leq t2 - t1 \leq 3.0 \quad (I),$$

wherein t1 (min) represents a contactual polymerization start time of the dental aqueous adhesive composition (A) and the dental curable composition (B), and t2 (min) represents a polymerization start time of the dental curable composition (B).
(2) The dental adhesive material kit according to (1), wherein the dental aqueous adhesive composition (A) and the dental curable composition (B) have a maximum contactual polymerization rate $V_{max}$ of 40%/min or more.
(3) The dental adhesive material kit according to (1) or (2), wherein the dental curable composition (B) comprises a radical polymerizable monomer (b) containing no acidic group, a polymerization accelerator (c), a chemical polymerization initiator (f), a photopolymerization initiator (g), and a filer (h).
(4) The dental adhesive material kit according to any one of (1) to (3), wherein the dental aqueous adhesive composition (A) comprises a radical polymerizable monomer (a) containing an acidic group, a radical polymerizable monomer (b-1) containing no amino group and no acidic group, a polymerization accelerator (c), and water (d).
(5) The dental adhesive material kit according to (3) or (4), wherein the polymerization accelerator (c) in the dental aqueous adhesive composition (A) and/or the polymerization accelerator (c) in the dental curable composition (B) comprise a period 4 transition metal compound (c-3).

(6) The dental adhesive material kit according to (5), wherein the polymerization accelerator (c) in the dental curable composition (B) comprises a period 4 transition metal compound (c-3), and the period 4 transition metal compound (c-3) comprises a vanadium compound (c-3-1) and a copper compound (c-3-2), the dental curable composition (B) having a vanadium compound (c-3-1) content of 0.01 to 0.04 parts by mass, and a copper compound (c-3-2) content of 0.001 to 0.0025 parts by mass relative to 100 parts by mass of the radical polymerizable monomer (b) containing no acidic group contained in the dental curable composition (B).

(7) The dental adhesive material kit according to any one of (1) to (6), wherein t1 (min) is more than 0.1 minutes and 3.0 minutes or less.

(8) The dental adhesive material kit according to any one of (1) to (7), wherein t2 (min) is 1.0 minute or more and less than 4.0 minutes.

(9) The dental adhesive material kit according to any one of (1) to (8), wherein the dental curable composition (B) comprises a chemical polymerization initiator (f), and the chemical polymerization initiator (f) comprises a hydroperoxide.

(10) The dental adhesive material kit according to (5), wherein the polymerization accelerator (c) in the dental aqueous adhesive composition (A) comprises a period 4 transition metal compound (c-3), and the period 4 transition metal compound (c-3) comprises a vanadium compound (c-3-1) and/or a copper compound (c-3-2).

(11) The dental adhesive material kit according to any one of (3) to (10), wherein the polymerization accelerator (c) in the dental curable composition (B) comprises a thiourea compound (c-2).

(12) The dental adhesive material kit according to any one of (1) to (11), wherein the dental curable composition (B) is a two-pack type.

(13) The dental adhesive material kit according to any one of (1) to (12), wherein the dental adhesive material kit is a dental cement kit.

Advantageous Effects of Invention

The present invention provides a dental adhesive material kit having desirable adhesive properties for tooth structure, and that, while ensuring appropriate strength, enables easy removal of a marginal excess cement in a semi-cured state created by temporarily applying light to excess portions of cement with a photoirradiator in bonding a crown restoration to tooth structure.

DESCRIPTION OF EMBODIMENTS

Figure 1:
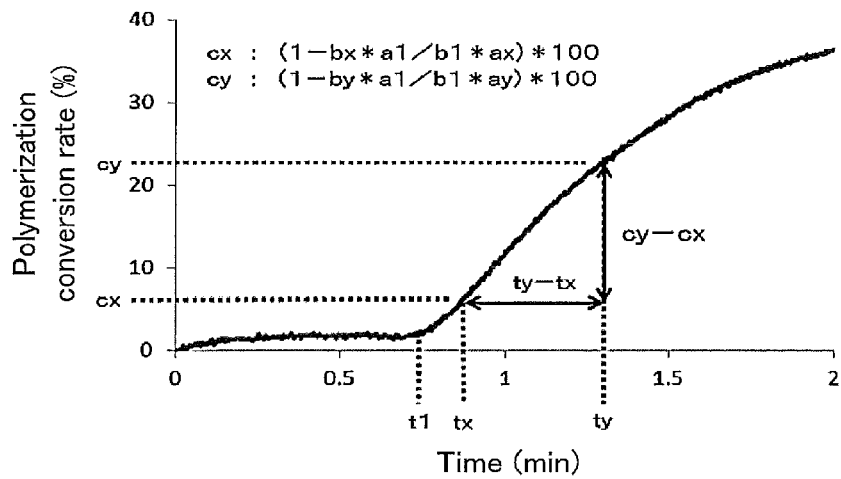
FIG. 1 is a diagram explaining a method of calculation of t1, t2, and $V_{max}$ for a dental adhesive material kit of the present invention.

The following specifically describes a dental adhesive material kit of the present invention.

It is important that a dental adhesive material kit of the present invention comprise a dental aqueous adhesive composition (A) and a dental curable composition (B), and satisfy the following formula (I)

$$0 \leq t2-t1 \leq 3.0 \tag{I},$$

wherein t1 (min) represents a contactual polymerization start time of the dental aqueous adhesive composition (A) and the dental curable composition (B), and t2 (min) represents a polymerization start time of the dental curable composition (B).

In the present invention, dental aqueous adhesive composition (A) means a surface treatment agent (primer) for tooth surface. In the present invention, dental curable composition (B) means a resin cement material for bonding a tooth structure and a prosthesis when used for a dental cement kit, a composite resin material for filling and restoring a tooth structure when used for a dental composite resin kit, and a bonding material for bonding a tooth structure and a composite resin when used for a dental adhesive material kit.

As used herein, contactual polymerization start time t1 means a time length before the polymerization conversion rate starts showing a large increase after the dental aqueous adhesive composition (A) and the dental curable composition (B) have come into contact with each other. As used herein, polymerization start time t2 means a time length before the polymerization conversion rate of the dental curable composition (B) starts showing a large increase. The contactual polymerization start time t1 and polymerization start time t2 can be measured using the methods described in the EXAMPLES section below.

The difference t2−t1 is not particularly limited. However, in view of reducing the difference in the extent of polymerization and for easy removal of the excess cement in a semi-cured state created by temporarily applying light with a photoirradiator, the difference t2−t1 is preferably 2.99 minutes or less, more preferably 2.95 minutes or less, even more preferably 2.90 minutes or less. In view of providing desirable adhesive properties and bond durability by increasing the effect of primer application for improved contact and bonding at the bond interface, the difference t2−t1 is 0 minute or more, preferably 0.2 minutes or more, more preferably 0.5 minutes or more, even more preferably 0.85 minutes or more.

In view of providing desirable adhesive properties and bond durability by increasing curability at the bond interface, the contactual polymerization start time t1 is preferably 3.0 minutes or less, more preferably 2.7 minutes or less, even more preferably 2.5 minutes or less. In view of improving ease of handling with a relative delay in curing after contact appropriate for making adjustments of prosthesis position after placement, t1 is preferably 0.1 minutes or more, more preferably 0.2 minutes or more, even more preferably 0.3 minutes or more. In view of increasing the mechanical strength of paste and providing desirable adhesive properties and bond durability by increasing paste curability and crosslink density, the polymerization start time t2 is preferably less than 6.0 minutes, more preferably 5.0 minutes or less, even more preferably 4.5 minutes or less. In view of improving ease of handling by providing appropriate time for the placement of a prosthesis after kneading the composition into a paste, t2 is preferably 1.0 minute or more, more preferably 1.5 minutes or more, even more preferably 2.0 minutes or more.

When a dental adhesive material kit of the present invention is used as a dental cement kit, it is preferable to use a dental aqueous adhesive composition (A) containing a polymerization accelerator (c) because the dental aqueous adhesive composition (A) can provide high adhesive properties for tooth structure when it contains a polymerization accelerator (c). However, when the dental aqueous adhesive composition (A) is containing a polymerization accelerator (c), the dental curable composition (B) polymerizes first in portions in contact with the dental aqueous adhesive composition (A) while the dental curable composition (B) remains unpolymerized in portions not in contact with the dental aqueous adhesive composition (A). That is, the extent of polymerization is different in these portions. This is problematic in removing a marginal excess cement (hereinafter, "excess cement") in a semi-cured state created by temporarily applying light to excess portions of cement with a photoirradiator in bonding a crown restoration to tooth structure. Specifically, with a short irradiation time, the excess cement remains completely unpolymerized at the surface, and the fluidity is too high to enable removal with a dental explorer, whereas the excess cement under longer exposure to light overly polymerizes in portions contacting the dental aqueous adhesive composition (A), and its removal becomes difficult to achieve. The present inventors have found that the dental curable composition (B) undergoes polymerization with a smaller difference in the extent of polymerization in portions contacting the dental aqueous adhesive composition (A) and in portions not contacting the dental aqueous adhesive composition (A), and the excess cement can be removed in one piece with ease when the dental adhesive material kit satisfies the formula (I) above in removing the excess cement in a semi-cured state created by temporarily applying light with a photoirradiator.

A dental adhesive material kit of the present invention can satisfy the formula (I) by, for example, combining specific catalysts in specific proportions. In this way, a dental curable composition (B) of the present invention can have a longer contactual polymerization start time t1 when in contact with the dental aqueous adhesive composition (A), and a shorter polymerization start time t2 for the chemical polymerization of the dental curable composition (B) itself without essentially affecting the final polymerization conversion rate, making it possible to provide appropriate strength, and enabling easier removal of excess cement in a semi-cured state created by temporarily applying light with a photoirradiator. Though it remains somewhat unclear how this takes place, the following describes a possible mechanism, taking specific catalyst systems as an example.

A ternary catalyst system involving a period 4 transition metal compound, a hydroperoxide, and a thiourea compound initiates polymerization under the following mechanism. First, low-valence transition metal ions in oxidized state are coordinated to the hydroperoxide, cleaving the hydroperoxide group and generating hydroxy anions, high-valence transition metal ions, and radicals. By being reduced by the thiourea compound, the high-valence transition metal ions regenerate oxidized low-valence transition metal ions, maintaining the polymerization rate constant. Here, the reaction rate by which the hydroperoxide and the period 4 transition metal form a coordination compound depends on the type of the period 4 transition metal used.

In a dental curable composition (B) using a catalyst system involving a vanadium compound, a hydroperoxide, and a thiourea compound, higher energy (activation energy) is required for the vanadium compound and the hydroperoxide to form a coordination compound, and polymerization takes longer to start. However, polymerization starts earlier when the dental curable composition (B) is in contact with a dental aqueous adhesive composition (A) containing a period 4 transition metal compound, and, once the vanadium compound and the hydroperoxide have formed a coordination compound, hydrogen abstraction can easily take place, and the vigorous generation of radicals actively initiates polymerization. That is, a dental curable composition (B) using only a vanadium compound as a period 4 transition metal compound starts polymerizing earlier when in contact with the dental aqueous adhesive composition (A), and, once polymerization starts, becomes completely cured at once. This makes it difficult to remove the excess cement.

A catalyst system involving a copper compound, a hydroperoxide, and a thiourea compound is characterized by low activation energy and a short time to start polymerization. Another characteristic is that hydrogen abstraction gradually proceeds. Accordingly, this catalyst system enables easy removal of excess cement of dental curable composition (B) after contact with the dental aqueous adhesive composition (A), compared to the catalyst system involving a vanadium compound, a hydroperoxide, and a thiourea compound. However, because the catalyst system involving a copper compound, a hydroperoxide, and a thiourea compound has a slow polymerization rate, and the polymerization rate is slow even after contact with the dental aqueous adhesive composition (A), the resultant cured product tends to have poor crosslink density, and weak adhesive properties for tooth structure.

Against this backdrop, the present inventors conducted intensive studies directed to reducing the difference in the extent of polymerization of excess cement before and after contact with the dental aqueous adhesive composition (A), and found that the difference between the polymerization start time t2 of dental curable composition (B) and the contactual polymerization start time t1 of dental aqueous adhesive composition (A) and dental curable composition (B) can be controlled within a range of 3 minutes or less by blending a vanadium compound and a copper compound in specific proportions. The specific mechanism is probably as follows. The hydroperoxide in dental curable composition (B) preferentially coordinates to the copper compound in portions of dental curable composition (B) contacting the dental aqueous adhesive composition (A), and polymerization initially proceeds at a gradual rate. This is followed by instantaneous polymerization initiated and driven by a coordination compound of the vanadium compound and the hydroperoxide. In this way, the dental curable composition (B) can have a longer polymerization start time for chemical polymerization when in contact with the dental aqueous adhesive composition (A), without essentially affecting the final polymerization conversion rate. In portions not in contact with the dental aqueous adhesive composition (A), the polymerization of dental curable composition (B) is initiated by a lower-activation-energy catalyst system involving a copper compound, a hydroperoxide, and a thiourea compound, and the dental curable composition (B) can have a shorter polymerization start time.

Preferably, a dental adhesive material kit of the present invention has a maximum contactual polymerization rate $V_{max}$ of at least 40%/min for dental aqueous adhesive composition (A) and dental curable composition (B). With a maximum contactual polymerization rate $V_{max}$ of at least 40%/min, a strong adhesive layer with high crosslink density can be obtained, and the adhesive properties and bond durability for tooth structure improve. In view of providing enough time for removal of excess cement, the maximum contactual polymerization rate $V_{max}$ is preferably at most 300%/min, more preferably at most 200%/min, even more preferably at most 100%/min. The maximum contactual polymerization rate $V_{max}$ can be measured by using the method described in the EXAMPLES section below.

The following specifically describes the components of a dental adhesive material kit of the present invention. It is preferable in a dental adhesive material kit of the present invention that the dental aqueous adhesive composition (A) comprise a radical polymerizable monomer (a) containing an acidic group, a radical polymerizable monomer (b-1) containing no amino group and no acidic group, a polymerization accelerator (c), and water (d). Preferably, the dental curable composition (B) comprises a radical polymerizable monomer (b) containing no acidic group, a polymerization accelerator (c), a chemical polymerization initiator (f), a photopolymerization initiator (g), and a filler (h).

The dental aqueous adhesive composition (A) is described first in detail.

Preferably, the dental aqueous adhesive composition (A) in the present invention comprises a radical polymerizable monomer (a) containing an acidic group. The radical polymerizable monomer (a) containing an acidic group promotes chemical polymerization at the bond interface, in addition to promoting demineralization of tooth structure and improving the adhesive properties for tooth structure. As used herein, "(meth)acryl" means methacryl or acryl, and "(meth) acryloyl" means methacryloyl or acryloyl.

Examples of the radical polymerizable monomer (a) containing an acidic group include a (meth)acrylic polymerizable monomer having at least one acidic group such as a phosphoric acid group, a pyrophosphoric acid group, a thiophosphoric acid group, a phosphonic acid group, a carboxylic acid group, and a sulfonic acid group, and at least one acryloyl group or methacryloyl group. The radical polymerizable monomer (a) containing an acidic group may be used alone, or two or more thereof may be used in combination as appropriate. Specific examples of the radical polymerizable monomer (a) containing an acidic group are as follows.

Examples of (meth)acrylic polymerizable monomers containing a phosphoric acid group include:

monofunctional (meth)acrylic acid esters containing a phosphoric acid group, such as 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, 2-(meth)acryloyloxyethylphenyl hydrogen phosphate, 2-(meth)acryloyloxyethyl-2-bromoethyl hydrogen phosphate, 2-methacryloyloxyethyl-(4-methoxyphenyl)hydrogen phosphate, and 2-methacryloyloxypropyl-(4-methoxyphenyl)hydrogen phosphate, and acid chlorides, alkali metal salts, and amine salts of these; and bifunctional (meth)acrylic acid esters containing a phosphoric acid, such as bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, and 1,3-di(meth)acryloyloxypropyl dihydrogen phosphate, and acid chlorides, alkali metal salts, and amine salts of these.

Examples of (meth)acrylic polymerizable monomers containing a pyrophosphoric acid group include bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth)acryloyloxyoctyl]pyrophosphate, bis[10-(meth)acryloyloxydecyl]pyrophosphate, and acid chlorides, alkali metal salts, and amine salts of these.

Examples of (meth)acrylic polymerizable monomers containing a thiophosphoric acid group include 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, 20-(meth)acryloyloxyeicosyl dihydrogen thiophosphate, and acid chlorides, alkali metal salts, and ammonium salts of these.

Examples of (meth)acrylic polymerizable monomers containing a phosphonic acid group include 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexylphosphonoacetate, 10-(meth)acryloyloxydecylphosphonoacetate, and acid chlorides, alkali metal salts, and ammonium salts of these.

Examples of (meth)acrylic polymerizable monomers containing a carboxylic acid group include monofunctional polymerizable monomers having one carboxyl group or acid anhydride group thereof within the molecule; and monofunctional polymerizable monomers having a plurality of carboxyl groups or acid anhydride groups thereof within the molecule.

Examples of monofunctional polymerizable monomers having one carboxyl group or acid anhydride group thereof within the molecule include (meth)acrylic acid, N-(meth)acryloylglycine, N-(meth)acryloylaspartic acid, 2-(meth)acryloyloxyethyl hydrogen succinate, 2-(meth)acryloyloxyethyl hydrogen phthalate, 2-(meth)acryloyloxyethyl hydrogen malate, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, and compounds replacing the carboxyl groups of these compounds with acid anhydride groups.

Examples of monofunctional polymerizable monomers having a plurality of carboxyl groups or acid anhydride groups thereof within the molecule include 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyltrimellitate, 4-(meth)acryloyloxyethyltrimellitate anhydride, 4-(meth)acryloyloxybutyltrimellitate, 4-(meth)acryloyloxyhexyltrimellitate, 4-(meth)acryloyloxydecyltrimellitate, 2-(meth)acryloyloxyethyl-3'-(meth)acryloyloxy-2'-(3,4-dicarboxybenzoyloxy)propylsuccinate, 6-(meth)acryloyloxyethylnaphthalene-1,2,6-tricarboxylic acid anhydride, 6-(meth)acryloyloxyethylnaphthalene-2,3,6-tricarboxylic acid anhydride, 4-(meth)acryloyloxyethylcarbonylpropionoyl-1,8-naphthalic acid anhydride, and 4-(meth)acryloyloxyethylnaphthalene-1,8-tricarboxylic acid anhydride.

Examples of (meth)acrylic polymerizable monomers containing a sulfonic acid group include 2-(meth)acrylamide-2-methylpropanesulfonic acid, and 2-sulfoethyl(meth)acrylate.

In view of providing desirable bond strength when used as a dental aqueous adhesive composition, the radical polymerizable monomer (a) containing an acidic group is preferably one or more selected from the group consisting of 10-(meth)acryloyloxydecyl dihydrogen phosphate, 4-(meth)acryloyloxyethyltrimellitate anhydride, 4-(meth)acryloyloxyethyltrimellitate, 11-(meth)acryloyloxyundecane-1,1-dicarboxylic acid, and a mixture of 2-methacryloyloxyethyl dihydrogen phosphate and bis(2-methacryloyloxyethyl)hydrogen phosphate.

The content of the radical polymerizable monomer (a) containing an acidic group in the dental aqueous adhesive composition (A) is preferably 1 to 45 parts by mass, more preferably 5 to 40 parts by mass, even more preferably 10 to 38 parts by mass relative to total 100 parts by mass of the radical polymerizable monomers and solvent contained in the dental aqueous adhesive composition (A). Here, the total of radical polymerizable monomers and solvent means a total amount of radical polymerizable monomer (a) containing an acidic group, water (d), organic solvent, and other polymerizable monomers (for example, a radical polymerizable monomer (b-1) containing no amino group and no acidic group).

Preferably, the dental aqueous adhesive composition (A) in the present invention comprises a radical polymerizable monomer (b-1) containing no amino group and no acidic group. The radical polymerizable monomer (b-1) containing no amino group and no acidic group means a radical polymerizable monomer that does not contain an amino group, and that does not contain an acidic group (such as a phosphoric acid group, a pyrophosphoric acid group, a thiophosphoric acid group, a phosphonic acid group, a carboxylic acid group, and a sulfonic acid group). Examples of the radical polymerizable monomer (b-1) containing no amino group and no acidic group include (meth)acrylic acid, (meth)acrylic acid esters, (meth)acrylamide, and derivatives of (meth)acrylamide.

The radical polymerizable monomer (b-1) containing no amino group and no acidic group can be broadly classified into aliphatic radical polymerizable monomer and aromatic radical polymerizable monomer. The radical polymerizable monomer (b-1) containing no amino group and no acidic group may be monofunctional, bifunctional, or tri- and higher-functional. As used herein, "monofunctional", "bifunctional", and "tri- and higher-functional" mean having one, two, and three or more radical polymerizable groups, respectively. In the following, "methacryloyl" and "acryloyl" will be collectively referred to as "(meth)acryloyl".

Specific examples of monofunctional aliphatic radical polymerizable monomers include methyl(meth)acrylate, ethyl(meth)acrylate, propyl(meth)acrylate, butyl(meth)acrylate, isobutyl(meth)acrylate, lauryl(meth)acrylate, 2,3-dibromopropyl(meth)acrylate, methoxypolyethylene glycol (meth)acrylate, glycidyl(meth)acrylate, 2-hydroxyethyl (meth)acrylate, 3-hydroxypropyl(meth)acrylate, 3-chloro-2-hydroxypropyl(meth)acrylate, tetrahydrofurfuryl(meth)acrylate, (meth)acryloylmorpholine, and diethyl(meth)acrylamide. Specific examples of bifunctional aliphatic radical polymerizable monomers include erythritol di(meth)acrylate, sorbitol di(meth)acrylate, mannitol di(meth)acrylate, pentaerythritol di(meth)acrylate, dipentaerythritol di(meth)acrylate, glycerol di(meth)acrylate, 1,2-bis(3-methacryloyloxy-2-hydroxypropoxy)ethane, ethylene glycol di(meth)acrylate, diethylene glycol di(meth)acrylate, triethylene glycol di(meth)acrylate, polyethylene glycol di(meth)acrylate, propylene glycol di(meth)acrylate, butylene glycol di(meth)acrylate, neopentyl glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 2,2,4-trimethylhexamethylenebis(2-carbamoyloxyethyl)dimethacrylate (commonly known as "UDMA"), tricyclodecanedimethanol di(meth)acrylate, ethylenebis(meth)acrylamide, propylenebis(meth)acrylamide, butylenebis(meth)acrylamide, N,N'-(dimethyl)ethylenebis (meth)acrylamide, N,N'-diethyl-1,3-propylenebis(meth)acrylamide, bis[2-(2-methyl-(meth)acrylamino)ethoxycarbonyl]hexamethylenediamine, and 2,2,4-trimethylhexamethylene-1,6-bis(meth)acrylamide. Specific examples of tri- and higher-functional aliphatic radical polymerizable monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol tri(meth)acrylate, dipentaerythritol tetra(meth)acrylate, dipentaerythritol penta(meth)acrylate, N,N-(2,2,4-trimethylhexamethylene)bis[2-(aminocarboxy)propane-1,3-diol]tetramethacrylate, and 1,7-diacryloyloxy-2,2,6,6-tetraacryloyloxymethyl-4-oxyheptane.

Examples of monofunctional aromatic radical polymerizable monomers include benzyl(meth)acrylate, phenoxyethyl(meth)acrylate, phenoxydiethylene glycol(meth)acrylate, phenoxypolyethylene glycol(meth)acrylate, 2-hydroxy-3-phenoxypropyl(meth)acrylate, 2-(meth)acryloyloxyethyl-2-hydroxyethyl-phthalic acid, and a neopentyl glycol-(meth)acrylic acid-benzoic acid ester. Examples of bifunctional aromatic radical polymerizable monomers include 2,2-bis[4-(3-(meth)acryloyloxy-2-hydroxypropoxy)phenyl]propane, 2,2-bis[4-(4-(meth)acryloyloxy-3-hydroxybutoxy)phenyl]propane, 2,2-bis[4-(4-(meth)acryloyloxy-2-hydroxybutoxy)phenyl]propane, 2,2-bis[4-(5-(meth)acryloyloxy-4-hydroxypentoxy)phenyl]propane, 2,2-bis((meth)acryloyloxyphenyl)propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxypolyethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, 2,2-bis(4-(meth)acryloyloxydipropoxyphenyl)propane, and 2,2-bis(4-(meth)acryloyloxyisopropoxyphenyl)propane. Examples of tri- and higher-functional aromatic radical polymerizable monomers include pentaerythritol tri(meth)acrylate. In the present invention, the radical polymerizable monomer (b-1) containing no amino group and no acidic group may be one of these compounds used alone, or two or more of these compounds used in combination.

In the present invention, the radical polymerizable monomer (b-1) containing no amino group and no acidic group is preferably a hydrophilic radical polymerizable monomer (b-1-1) containing no amino group and no acidic group because such a hydrophilic radical polymerizable monomer penetrates into tooth structure, and improves adhesion by increasing the degree of polymerization of the cured product. The hydrophilic radical polymerizable monomer (b-1-1) containing no amino group and no acidic group is preferably a monofunctional hydrophilic radical polymerizable monomer containing no amino group and no acidic group. In view of the effect to improve penetration into the collagen layer of dentin, the hydrophilic radical polymerizable monomer (b-1-1) containing no amino group and no acidic group is preferably 2-hydroxyethyl(meth)acrylate, 3-hydroxypropyl(meth)acrylate, glycerol mono(meth)acrylate, erythritol mono(meth)acrylate, methoxypolyethylene glycol (meth)acrylate, (meth)acryloylmorpholine, or diethyl(meth)acrylamide, particularly preferably 2-hydroxyethyl methacrylate.

The content of the radical polymerizable monomer (b-1) containing no amino group and no acidic group in the dental aqueous adhesive composition (A) is preferably 25 to 70 parts by mass, more preferably 28 to 60 parts by mass, even more preferably 30 to 50 parts by mass relative to total 100 parts by mass of the radical polymerizable monomers and solvent contained in the dental aqueous adhesive composition (A). With at least 25 parts by mass of radical polymerizable monomer (b-1) containing no amino group and no acidic group, the dental aqueous adhesive composition (A) can more prominently produce the adhesive property improving effect obtained by containing this monomer. With at most 70 parts by mass of radical polymerizable monomer (b-1) containing no amino group and no acidic group, the dental aqueous adhesive composition (A) can develop its ability to demineralize tooth structure at high level without losing the effect produced by the radical polymerizable monomer (b-1) containing no amino group and no acidic group.

In the present invention, the dental aqueous adhesive composition (A) may contain a radical polymerizable monomer (b-2) containing an amino group but no acidic group. Specific examples of the radical polymerizable monomer (b-2) containing an amino group but no acidic group include 2-(dimethylamino)ethyl (meth)acrylate, 2-(diethylamino)ethyl (meth)acrylate, 2-(dipropylamino)ethyl (meth)acrylate, 6-(diethylamino)hexyl (meth)acrylate, 6-(dimethylamino)hexyl (meth)acrylate, N-methyldiethanolamine di(meth)acrylate, and triethanolamine di(meth)acrylate. These may be used alone, or two or more thereof may be used in combination. In view of desirable curability, 2-(dimethylamino)ethyl methacrylate is most preferred. The radical polymerizable monomer (b-2) containing an amino group but no acidic group is a component for adjusting the pH of dental aqueous adhesive composition (A). The radical polymerizable monomer (b-2) containing an amino group but no acidic group inhibits excessive demineralization, and enables demineralization that is appropriate for penetration and cure, particularly when applied to dentin. Additionally, the radical polymerizable monomer (b-2) containing an amino group but no acidic group improves the storage stability of dental aqueous adhesive composition (A). The dental aqueous adhesive composition (A) has a pH of preferably less than 4.0, more preferably 1.2 to 3.5, even more preferably 1.5 to 3.0. Preferably, the content of radical polymerizable monomer (b-2) containing an amino group but no acidic group is adjusted to achieve these pH values. The pH can be measured with a known measurement device, for example, such as a LAQUAtwin manufactured by HORIBA Ltd.

In the present invention, the dental aqueous adhesive composition (A) preferably contains a polymerization accelerator (c). The polymerization accelerator (c) is a component that acts as a reducing agent for redox polymerization. Examples of the polymerization accelerator (c) in the dental aqueous adhesive composition (A) include an aromatic amine (c-1) having no electron withdrawing group on the aromatic ring, a thiourea compound (c-2), and a period 4 transition metal compound (c-3). The polymerization accelerator (c) in the dental aqueous adhesive composition (A) may be used alone, or two or more thereof may be used in combination. A certain preferred embodiment is a dental adhesive material kit that comprises a dental aqueous adhesive composition (A) and a dental curable composition (B), and in which the dental aqueous adhesive composition (A) comprises a polymerization accelerator (c), and the polymerization accelerator (c) is at least one selected from the group consisting of an aromatic amine (c-1) having no electron withdrawing group on the aromatic ring, a thiourea compound (c-2), and a period 4 transition metal compound (c-3). The polymerization accelerator (c) contained in the dental aqueous adhesive composition (A) may be a borate compound such as an arylborate compound; or a transition metal compound (c-4) other than period 4 transition metal compounds. However, it is not necessarily required to contain these components. For improved polymerization accelerating effect, the polymerization accelerator (c) preferably comprises a period 4 transition metal compound (c-3).

Examples of the aromatic amine (c-1) having no electron withdrawing group on the aromatic ring include N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, and N,N-dimethyl-3,5-di-t-butylaniline. The aromatic amine (c-1) having no electron withdrawing group on the aromatic ring may be used alone, or two or more thereof may be used in combination.

Examples of the thiourea compound (c-2) include thiourea, methylthiourea, ethylthiourea, ethylenethiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, tetracyclohexylthiourea, 1-(2-pyridyl)-2-thiourea, and 4,4-dimethylethylenethiourea.

The period 4 transition metal compound (c-3) may be a vanadium compound (c-3-1), a copper compound (c-3-2), or a period 4 transition metal compound (c-3-3) other than vanadium compounds and copper compounds. For improved polymerization accelerating effect, the polymerization accelerator (c) in the present invention preferably comprises a vanadium compound (c-3-1) and/or a copper compound (c-3-2). Examples of the vanadium compound (c-3-1) include vanadium acetylacetonate, vanadyl acetylacetonate, vanadyl stearate, vanadium naphthenate, vanadium benzoylacetonate, vanadyl oxalate, bis(maltolato)oxovanadium(IV), vanadium(IV) oxobis(1-phenyl-1,3-butanedionate), vanadium(V)oxytriisopropoxide, ammonium metavanadate, sodium metavanadate, vanadium(V) oxide, vanadium(IV) oxide, and vanadyl sulfate. In view of properties such as solubility in solvent, preferred are vanadium acetylacetonate, vanadyl acetylacetonate, and bis(maltolato)oxovanadium(IV), and more preferred are vanadyl acetylacetonate and bis(maltolato)oxovanadium(IV). The vanadium compound (c-3-1) may be used alone, or two or more thereof may be used in combination. The copper compound (c-3-2) is preferably, for example, a compound soluble in radical polymerizable monomers. Specific examples of such compounds include:

copper carboxylates, such as copper acetate, copper isobutyrate, copper gluconate, copper citrate, copper phthalate, copper tartarate, copper oleate, copper octylate, copper octenoate, copper naphthenate, copper methacrylate, and copper 4-cyclohexylbutyrate;

β-diketone-copper, such as copper acetylacetonate, copper trifluoroacetylacetonate, copper hexafluoroacetylacetonate, copper 2,2,6,6-tetramethyl-3,5-heptanedionate, and copper benzoylacetone;

β-ketoester-copper, such as copper ethylacetoacetate;

copper alkoxides, such as copper methoxide, copper ethoxide, copper isopropoxide, copper 2-(2-butoxyethoxy) ethoxide, and copper 2-(2-methoxyethoxy)ethoxide;

copper dithiocarbamates, such as copper dimethyldithiocarbamate;

salts of copper and inorganic acids, such as copper nitrate; and copper chloride.

These may be used alone, or two or more thereof may be used in combination as appropriate. In view of solubility and reactivity to radical polymerizable monomers, preferred are copper carboxylates, β-diketone-copper, and β-ketoester-copper, and particularly preferred are copper acetate and copper acetylacetonate. Examples of the period 4 transition metal compound (c-3-3) include scandium isopropoxide, iron(III) ethoxide, titanium methoxide, titanium ethoxide, titanium isopropoxide, titanium butoxide, titanium hydroxide, and titanium fluoride. The polymerization accelerator (c) may comprise a transition metal compound (c-4) other than period 4 transition metal compounds. Examples of the transition metal compound (c-4) include strontium carbonate, strontium hydroxide, strontium ethoxide, tin(II) methoxide, indium ethoxide, actinium ethoxide, yttrium isopropoxide, lanthanum methoxide, lanthanum ethoxide, lanthanum isopropoxide, lanthanum butoxide, lanthanum hydroxide, lanthanum carbonate, lanthanum fluoride, cerium isopropoxide, praseodymium isopropoxide, promethium isopropoxide, neodymium isopropoxide, samarium isopropoxide, europium isopropoxide, gadolinium isopropoxide, terbium ethoxide, terbium methoxide, dysprosium isopropoxide, holmium isopropoxide, erbium isopropoxide, thulium isopropoxide, ytterbium isopropoxide, zirconium ethoxide, zirconium isopropoxide, zirconium butoxide, tungsten(IV) methoxide, tungsten(IV) isopropoxide, and tungsten(IV) butoxide. Preferred for use as period 4 transition metal compound (c-3) are, for example, vanadium(IV) oxide, vanadyl(IV) acetylacetonate, vanadyl oxalate, vanadyl sulfate, vanadium(IV) oxobis(1-phenyl-1,3-butanedionate), bis(maltolato)oxovanadium(IV), vanadium(V) oxide, sodium metavanadate, and ammonium metavanadate. In view of improved polymerization accelerating effect, vanadyl(IV) acetylacetonate and bis(maltolato)oxovanadium(IV) are preferred, and vanadyl(IV) acetylacetonate is most preferred. The polymerization accelerator (c) may be used alone, or two or more thereof may be used in combination.

In order to prevent a delay in curing, the content of the polymerization accelerator (c) in the dental aqueous adhesive composition (A) is preferably at least 0.0001 parts by mass, more preferably at least 0.0005 parts by mass, even more preferably at least 0.001 parts by mass relative to 100 parts by mass of the radical polymerizable monomers contained in the dental aqueous adhesive composition (A). In view of storage stability, the content of the polymerization accelerator (c) in the dental aqueous adhesive composition (A) is preferably at most 10 parts by mass, more preferably at most 5.0 parts by mass, even more preferably at most 2.0 parts by mass.

In the present invention, the dental aqueous adhesive composition (A) preferably comprises water (d). Water (d) contributes to promoting penetration of the composition into tooth structure. Water (d) also serves to dissolve the radical polymerizable monomer (a) containing an acidic group, and the polymerization accelerator (c), providing a field for the dissolution and reaction of substances that contribute to initiate polymerization.

The content of water (d) in the dental aqueous adhesive composition (A) is preferably 5 to 75 parts by mass, more preferably 10 to 60 parts by mass, even more preferably 15 to 45 parts by mass relative to total 100 parts by mass of the radical polymerizable monomers and solvent contained in the dental aqueous adhesive composition (A).

In the present invention, the dental aqueous adhesive composition (A) may comprise a polymerization inhibitor to impart storage stability. The polymerization inhibitor in the dental aqueous adhesive composition (A) inhibits discoloration of dental aqueous adhesive composition (A) and decrease of the adhesive properties of dental aqueous adhesive composition (A), and provides desirable storage stability. Examples of the polymerization inhibitor include phenol-based compounds, phosphorus-based compounds, sulfur-based compounds, and amine-based compounds. Preferred are phenol-based compounds. Specific examples include hydroquinone, hydroquinone monomethyl ether, 3,5-di-t-butyl-4-hydroxytoluene, 3,5-di-t-butyl-4-hydroxyanisole, and 4-t-butyl pyrocatechol. Preferred for use are hydroquinone monomethyl ether and 3,5-di-t-butyl-4-hydroxytoluene because these do not interfere with adhesive properties, and have a strong effect to reduce discoloration and gelation.

In the present invention, the dental aqueous adhesive composition (A) may comprise a photopolymerization initiator to impart photocurability.

In the present invention, the dental aqueous adhesive composition (A) may comprise a filler (h) to improve spreadability and fluidity. In view of spreadability and fluidity, the filler (h) is preferably a fine particle filler having an average primary particle diameter of 1 nm to 0.1 μm. Specific examples of such fillers include Aerosil® OX50, Aerosil® 50, Aerosil® 200, Aerosil® 380, Aerosil® R972, and Aerosil® 130 (all manufactured by Nippon Aerosil Co., Ltd.). The average primary particle diameter can be measured using the same method used for filler (h) of dental curable composition (B).

In order to improve adhesion, spreadability, and penetration into tooth structure, and to improve the solubility of the radical polymerizable monomer (a) containing an acidic group and the radical polymerizable monomer (b-1) containing no amino group and no acidic group in water (d), the dental aqueous adhesive composition (A) of the present invention may comprise a water-soluble organic solvent. The water-soluble organic solvent is typically an organic solvent having a boiling point of 150° C. or less under ordinary pressure, and a solubility in water at 25° C. of at least 5 mass %, more preferably at least 30 mass %, most preferably a solubility that enables the solvent to dissolve in water in any desired fractions. Preferred is a water-soluble organic solvent having a boiling point of 100° C. or less under ordinary pressure. Specific examples of such water-soluble organic solvents include ethanol, methanol, 1-propanol, isopropyl alcohol, acetone, methyl ethyl ketone, 1,2-dimethoxyethane, 1,2-diethoxyethane, and tetrahydrofuran.

In order to eliminate the need for mixing and to simplify the procedure, the dental aqueous adhesive composition (A) in a dental adhesive material kit of the present invention is preferably a one-pack type.

The following describes the dental curable composition (B).

In the present invention, the dental curable composition (B) preferably comprises a radical polymerizable monomer (b) containing no acidic group. Specific examples of the radical polymerizable monomer (b) containing no acidic group include the radical polymerizable monomer (b-1) containing no amino group and no acidic group and the radical polymerizable monomer (b-2) containing an amino group but no acidic group used for the dental aqueous adhesive composition (A).

In view of good wettability for the dental aqueous adhesive composition (A) and high adhesive properties for tooth structure, 1,2-bis(3-methacryloyloxy-2-hydroxypropoxy)ethane is preferred. In view of providing high mechanical strength for the cured product, 2,2-bis[4-(3-methacryloyloxy-2-hydroxypropoxy)phenyl]propane, and 2,2-bis(4-methacryloyloxypolyethoxyphenyl)propane (average number of moles of ethoxy groups added: 2.6) are preferred.

The content of the radical polymerizable monomer (b) containing no acidic group in dental curable composition (B) is preferably 15 to 99.5 parts by mass relative to total 100 parts by mass of the radical polymerizable monomers and fillers in the dental curable composition (B). With a radical polymerizable monomer content of less than 15 parts by mass, the viscosity of dental curable composition (B) may overly increase, and ease of handling may decrease. In this case, it may not be possible to adjust viscosity or to improve the mechanical strength of dental curable composition (B) upon cure even when a filler is added to produce these effects. Likewise, with a radical polymerizable monomer content of more than 99.5 parts by mass, it may not be possible to adjust viscosity or to improve the mechanical strength of dental curable composition (B) upon cure even when a filler is added to produce these effects. The dental curable composition (B) of the present invention can be suitably used as, for example, a dental bonding material, a dental composite resin, or a dental resin cement. In view of the viscosity of dental curable composition (B) and the mechanical strength of dental curable composition (B) upon cure, the radical polymerizable monomer content of when the dental curable composition (B) is used as a dental composite resin or dental resin cement is preferably 15 to 60 parts by mass, more preferably 19 to 50 parts by mass, even more preferably 24 to 48 parts by mass relative to total 100 parts by mass of the radical polymerizable monomer (b) containing no acidic group and the fillers contained in the dental curable composition (B).

In the present invention, the dental curable composition (B) preferably comprises a polymerization accelerator (c). Specific examples of the polymerization accelerator (c) include the same polymerization accelerators used for the dental aqueous adhesive composition (A). A certain preferred embodiment is a dental adhesive material kit that comprises a dental aqueous adhesive composition (A) and a dental curable composition (B), and in which the dental curable composition (B) comprises a polymerization accelerator (c), and the polymerization accelerator (c) is at least one selected from the group consisting of an aromatic amine (c-1) having no electron withdrawing group on the aromatic ring, a thiourea compound (c-2), and a period 4 transition metal compound (c-3). The polymerization accelerator (c) contained in the dental curable composition (B) may be a borate compound such as an arylborate compound; or a transition metal compound (c-4) other than period 4 transition metal compounds. However, it is not necessarily required to contain these components.

In a dental adhesive material kit of the present invention, it is preferable that the polymerization accelerator (c) for redox polymerization comprise a thiourea compound (c-2) and a period 4 transition metal compound (c-3) in the dental curable composition (B). In certain embodiments, the dental curable composition (B) comprises preferably 0.01 to 0.04 parts by mass of vanadium compound (c-3-1), and 0.001 to 0.0025 parts by mass of copper compound (c-3-2), more preferably 0.02 to 0.035 parts by mass of vanadium compound (c-3-1), and 0.0015 to 0.0025 parts by mass of copper compound (c-3-2) relative to 100 parts by mass of the radical polymerizable monomers contained in the dental curable composition (B). When the content of vanadium compound (c-3-1) is too low, the vanadium compound (c-3-1) fails to produce its effect, and the maximum contactual polymerization rate $V_{max}$ of dental aqueous adhesive composition (A) and dental curable composition (B) takes a value of less than 40%/min. This may result in a dental adhesive material kit having reduced adhesive properties for tooth structure and reduced weak mechanical strength. When the content of vanadium compound (c-3-1) is too high, the contactual polymerization start time t1 of dental aqueous adhesive composition (A) and dental curable composition (B) tends to be shorter, and the dental curable composition (B), when used as a kit, has a possibility of becoming too hard in portions coming into contact with the dental aqueous adhesive composition (A). When the content of copper compound (c-3-2) is too low, the polymerization start time t2 of dental curable composition (B) tends to be longer, and the dental curable composition (B), when used as a kit, may fail to sufficiently cure in portions that are not in contact with the dental aqueous adhesive composition (A) at the time of temporary exposure to light. When the content of copper compound (c-3-2) is too high, the radical polymerizable monomers in the dental curable composition (B) tend to polymerize too easily, and the storage stability of dental curable composition (B) may decrease.

Specific examples of the polymerization accelerator (c) include the same polymerization accelerators used for the dental aqueous adhesive composition (A). Specifically, the content of vanadium compound (c-3-1) in dental curable composition (B) ranges preferably from 0.01 to 0.04 parts by mass, more preferably from 0.015 to 0.038 parts by mass, even more preferably from 0.02 to 0.035 parts by mass relative to 100 parts by mass of the radical polymerizable monomers contained in the dental curable composition (B). The content of copper compound (c-3-2) in dental curable composition (B) ranges preferably from 0.001 to 0.0030 parts by mass, more preferably from 0.0012 to 0.0028 parts by mass, even more preferably from 0.0015 to 0.0025 parts by mass relative to 100 parts by mass of the radical polymerizable monomers contained in the dental curable composition (B).

In the present invention, the dental curable composition (B) preferably comprises a chemical polymerization initiator (f). The chemical polymerization initiator (f) is a component representing an oxidizing agent for the redox polymerization initiator.

Examples of the chemical polymerization initiator (f) include organic peroxides, azo compounds, and inorganic peroxides. Examples of the organic peroxides include diacyl peroxides, peroxyesters, dialkyl peroxides, peroxyketals, ketone peroxides, and hydroperoxides. Specific examples of diacyl peroxides include benzoyl peroxide, 2,4-dichlorobenzoyl peroxide, and m-toluoyl peroxide. Specific examples of peroxyesters include t-butyl peroxybenzoate, bis(t-butylperoxy)isophthalate, 2,5-dimethyl-2,5-bis(benzoylperoxy) hexane, t-butyl peroxy-2-ethylhexanoate, and t-butyl peroxyisopropyl carbonate. Specific examples of dialkyl peroxides include dicumyl peroxide, di-t-butyl peroxide, and lauroyl peroxide. Specific examples of peroxyketals include 1,1-bis(t-butylperoxy)3,3,5-trimethylcyclohexane, 1,1-bis(t-butylperoxy)cyclohexane, and 1,1-bis(t-hexylperoxy)cyclohexane. Specific examples of ketone peroxides include methyl ethyl ketone peroxide, cyclohexanone peroxide, and methyl acetoacetate peroxide. Specific examples of hydroperoxides include t-butyl hydroperoxide, cumene hydroperoxide, p-diisopropylbenzene hydroperoxide, and 1,1,3,3-tetramethylbutyl hydroperoxide. Examples of the azo compounds include 2,2'-azobis(isobutyronitrile), 2,2'-azobis(2-methylbutyronitrile), 2,2'-azobis(2,4-dimethylvaleronitrile), and 2,2'-azobis(4-methoxy-2,4-dimethylvaleronitrile). Examples of the inorganic peroxides include sodium persulfate, potassium persulfate, aluminum persulfate, and ammonium persulfate.

In view of storage stability, preferred as chemical polymerization initiator (f) are hydroperoxides. In view of desirable polymerizability at the interface with tooth structure, 1,1,3,3-tetramethylbutyl hydroperoxide is particularly preferred.

The content of chemical polymerization initiator (f) in dental curable composition (B) is preferably 0.1 to 10 parts by mass relative to 100 parts by mass of the radical polymerizable monomers contained in the dental curable composition (B). Because a chemical polymerization initiator content of less than 0.1 parts by mass leads to a possible delay in curing, the content of chemical polymerization initiator (f) is more preferably at least 0.2 parts by mass, even more preferably at least 0.3 parts by mass. With a chemical polymerization initiator content of more than 10 parts by mass, the cure rate overly increases, and it may not be possible to obtain high adhesive properties. In this respect, the content of chemical polymerization initiator (f) is more preferably at most 7.5 parts by mass, even more preferably at most 5.0 parts by mass. Taken together, the content of chemical polymerization initiator (f) is more preferably 0.2 to 7.5 parts by mass, even more preferably 0.3 to 5.0 parts by mass relative to 100 parts by mass of the radical polymerizable monomers contained in the dental curable composition (B).

Examples of the photopolymerization initiator (g) in dental curable composition (B) include (bis)acylphosphine oxides and salts thereof, α-diketones, thioxanthones or quaternary ammonium salts of thioxanthones, ketals, coumarins, anthraquinones, benzoin alkyl ether compounds, and α-aminoketone compounds. Specific examples of these include the compounds mentioned in WO2008/087977. Examples of acylphosphine oxides in the (bis)acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di(2, 6-dimethylphenyl)phosphonate, and salts thereof (sodium salts, potassium salts, ammonium salts). Preferred are sodium salts of 2,4,6-trimethylbenzoylphenylphosphine oxide. Examples of bisacylphosphine oxides include bis(2, 6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, bis(2,5,6-trimethylbenzoyl)-2,4,4-trimethylpentylphosphine oxide, and salts thereof (sodium salts, potassium salts, ammonium salts). Examples of the α-diketones include diacetyl, benzyl, camphorquinone, 2,3-pentadione, 2,3-octadione, 9,10-phenanthrenequinone, 4,4'-oxybenzyl, and acenaphthenequinone. Particularly preferred is camphorquinone for its maximum absorption wavelength occurring in the visible light region.

The photopolymerization initiator (g) is preferably at least one selected from the group consisting of a (bis)acylphosphine oxide, a salt thereof, and an α-diketone. In this way, a composition can be provided that has desirable photocurability both in the visible light region and the near ultraviolet region, and that shows sufficient photocurability regardless of whether the light source used is a halogen lamp, a light emitting diode (LED), or a xenon lamp.

The content of photopolymerization initiator (g) in dental curable composition (B) is not particularly limited. However, in view of photocurability, the content of photopolymerization initiator (g) is preferably 0.01 to 10 parts by mass, more preferably 0.10 to 3.0 parts by mass relative to 100 parts by mass of the radical polymerizable monomers contained in the dental curable composition (B).

When used, the photopolymerization initiator (g) may be used with a known photopolymerization accelerator, in order to accelerate photopolymerization. That is, the dental curable composition (B) may comprise a photopolymerization accelerator.

Examples of the photopolymerization accelerator contained in dental curable composition (B) include amines, sulfinic acid and salts thereof, borate compounds, derivatives of barbituric acid, triazine compounds, tin compounds, copper compounds, halogen compounds, aldehydes, thiol compounds, sulfites, and bisulfites. The photopolymerization accelerator may be used alone, or two or more thereof may be used in combination. In certain embodiments, the dental curable composition (B) may not comprise a borate compound. In other embodiments, a dental adhesive material kit may be provided in which the dental curable composition (B) comprises a photopolymerization accelerator, and the photopolymerization accelerator is at least one selected from the group consisting of an amine, sulfinic acid, a salt of sulfinic acid, a derivative of barbituric acid, a triazine compound, a tin compound, a copper compound, a halogen compound, an aldehyde, a thiol compound, a sulfite, and a bisulfite.

Examples of amines as the photopolymerization accelerator include aliphatic amines and aromatic amines. It is to be noted that, in this specification, the radical polymerizable monomer containing an amino group but no acidic group is excluded from amines representing the polymerization accelerator (c).

Examples of aliphatic amines as the photopolymerization accelerator include primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, triethanolamine, trimethylamine, triethylamine, and tributylamine. In view of curability and storage stability of dental curable composition (B), tertiary aliphatic amines are preferred, and N-methyldiethanolamine and triethanolamine are more preferred.

Examples of aromatic amines as the photopolymerization accelerator include N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino)benzoate, propyl 4-(N,N-dimethylamino)benzoate, n-butoxyethyl 4-(N,N-dimethylamino)benzoate, 2-[(meth)acryloyloxy]ethyl 4-(N,N-dimethylamino)benzoate, 4-(N,N-dimethylamino)benzophenone, butyl 4-dimethylaminobenzoate, and 4-(dimethylamino)benzonitrile. In view of the ability to impart desirable curability to the composition, preferred is at least one selected from the group consisting of N,N-bis(2-hydroxyethyl)-p-toluidine, ethyl 4-(N,N-dimethylamino)benzoate, n-butoxyethyl 4-(N,N-dimethylamino)benzoate, and 4-(N,N-dimethylamino)benzophenone.

The content of the photopolymerization accelerator in the dental curable composition (B) is not particularly limited. However, in view of photocurability, the content of photopolymerization accelerator is preferably 0.01 to 5.0 parts by mass, more preferably 0.10 to 3.0 parts by mass relative to 100 parts by mass of the radical polymerizable monomers contained in the dental curable composition (B).

The filler (h) in dental curable composition (B) of the present invention can be broadly classified into inorganic filler, organic filler, and organic-inorganic composite filler.

Examples of materials of the inorganic filler include quartz, silica, alumina, silica-titania, silica-titania-barium oxide, silica-zirconia, silica-alumina, lanthanum glass, borosilicate glass, soda glass, barium glass, strontium glass, glass-ceramics, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These inorganic fillers may be used alone, or two or more thereof may be used as a mixture. The shape of inorganic filler is not particularly limited, and the particle size of filler may be appropriately selected. The inorganic filler has an average particle diameter of preferably 0.001 to 50 μm, more preferably 0.001 to 10 μm. The inorganic filler may be a combination of an ultrafine particle having an average particle diameter of 0.001 to 0.1 μm, and a macro particle having an average particle diameter of 1 to 50 μm (preferably 1 to 10 μm). The inorganic filler may be an irregularly shaped filler or a spherical filler, and these may be appropriately selected.

The inorganic filler may be used after an optional surface treatment with a known surface treatment agent such as a silane coupling agent. Examples of such surface treatment agents include vinyltrimethoxysilane, vinyltriethoxysilane, vinyltrichlorosilane, vinyltri(β-methoxyethoxy)silane, γ-methacryloyloxypropyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

Examples of materials of the organic filler include polymethyl methacrylate, polyethyl methacrylate, a methyl methacrylate-ethyl methacrylate copolymer, crosslinked polymethyl methacrylate, crosslinked polyethyl methacrylate, polyamides, polyvinyl chloride, polystyrene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. These may be used alone, or two or more thereof may be used in combination. The shape of organic filler is not particularly limited, and the particle size of filler may be appropriately selected. The organic filler has an average particle diameter of preferably 0.001 to 50 μm, more preferably 0.001 to 10 μm. The organic filler may be a combination of an ultrafine particle having an average particle diameter of 0.001 to 0.1 μm, and a macro particle having an average particle diameter of 1 to 50 μm (preferably 1 to 10 μm).

The organic-inorganic composite filler is a filler obtained by adding a monomer compound to the inorganic filler, and pulverizing the polymer obtained after polymerizing the filler mixture in paste form. Examples of the organic-inorganic composite filler include a TMPT filler (a filler obtained by mixing trimethylolpropane methacrylate and a silica filler, and pulverizing the mixture after polymerization). The shape of the organic-inorganic composite filler is not particularly limited, and the particle size of filler may be appropriately selected. The organic-inorganic composite filler has an average particle diameter of preferably 0.001 to 50 μm, more preferably 0.001 to 10 μm. The organic-inorganic composite filler may be a combination of an ultrafine particle having an average particle diameter of 0.001 to 0.1 μm, and a macro particle having an average particle diameter of 1 to 50 μm (preferably 1 to 10 μm).

In this specification, the average particle diameter of filler (h) means an average particle diameter of primary particles of filler (average primary particle diameter), and the average primary particle diameter can be determined using a laser diffraction scattering method or by observing particles with an electron microscope. Specifically, a laser diffraction scattering method is more convenient for the measurement of particles having an average particle diameter of 0.1 μm or more, whereas electron microscopy is a more convenient method of average particle diameter measurement for ultrafine particles of less than 0.1 μm. Here, 0.1 μm is a measured value by a laser diffraction scattering method.

For the measurement using a laser diffraction scattering method, for example, a laser diffraction particle size distribution analyzer (SALD-2300, manufactured by Shimadzu Corporation) may be used with a 0.2% sodium hexametaphosphate aqueous solution used as dispersion medium.

In electron microscopy, for example, particles may be photographed with a scanning electron microscope (Model S-4000, manufactured by Hitachi), and the size of particles (at least 200 particles) observed in a unit field of the micrograph may be measured using image-analyzing particle-size-distribution measurement software (Macview; Mountech Co., Ltd.). Here, the particle diameter is determined as an arithmetic mean value of the maximum and minimum lengths of particles, and the average primary particle diameter is calculated from the number of particles and the particle diameter.

In order to impart fluorine releasability to dental curable composition (B), it is preferable that the filler (h) be at least one selected from the group consisting of fluoroaluminosilicate glass, calcium fluoroaluminosilicate glass, strontium fluoroaluminosilicate glass, barium fluoroaluminosilicate glass, and strontium calcium fluoroaluminosilicate glass, more preferably fluoroaluminosilicate glass and/or barium fluoroaluminosilicate glass. In order to impart radiopacity to dental curable composition (B), it is preferable that the filler (h) be at least one selected from the group consisting of barium glass, strontium glass, barium boroaluminosilicate glass, strontium boroaluminosilicate glass, strontium fluoroaluminosilicate glass, and barium fluoroaluminosilicate glass, more preferably barium glass and/or barium fluoroaluminosilicate glass.

The content of filler (h) in dental curable composition (B) is preferably 0.5 to 85 parts by mass relative to total 100 parts by mass of the radical polymerizable monomers and fillers contained in the dental curable composition (B). With a filler (h) content of less than 0.5 parts by mass, it may not be possible to adjust the viscosity of dental curable composition (B) or to improve the mechanical strength of dental curable composition (B) upon cure even when the filler is added to produce these effects. With a filler (h) content of more than 85 parts by mass, the viscosity of dental curable composition (B) may overly increase, and ease of handling may decrease. A dental curable composition (B) of the present invention can be suitably used as, for example, a dental bonding material, a dental composite resin, or a dental curable composition (B), as will be described later. In view of the viscosity of dental curable composition (B) and the mechanical strength of dental curable composition (B) upon cure, the filler content of when the dental curable composition (B) is used as a dental composite resin or a dental curable composition (B) is preferably 40 to 85 parts by mass, more preferably 50 to 81 parts by mass, even more preferably 52 to 76 parts by mass relative to total 100 parts by mass of the radical polymerizable monomers and fillers contained in the dental curable composition (B).

In the present invention, the dental curable composition (B) may comprise a radical polymerizable monomer (a) containing an acidic group, in order to improve adhesive properties for tooth structure and prostheses, though this is not intended to limit the present invention to a particular type of dental curable composition (B). The radical polymerizable monomer (a) containing an acidic group may be the same radical polymerizable monomer (a) containing an acidic group exemplified above for the dental aqueous adhesive composition (A).

In the present invention, the dental curable composition (B) may comprise components such as polymerization inhibitors, ultraviolet absorbers, thickeners, colorants, antimicrobial agents, and fragrances, provided such additional components do not interfere with the effects of the present invention.

In view of storage stability, it is preferable in a dental adhesive material kit of the present invention that the dental curable composition (B) be a two-pack type (two-paste type). Specifically, the dental curable composition (B) preferably has a form separately packing a first agent (for example, a first paste) containing a hydroperoxide as chemical polymerization initiator (f), and a second agent (for example, a second paste) containing a thiourea compound (c-2) as polymerization accelerator (c). A preferred embodiment (X-1) of the present invention is, for example, a dental adhesive material kit comprising a dental aqueous adhesive composition (A) and a dental curable composition (B), wherein the dental curable composition (B) comprises a first agent and a second agent, and the first agent comprises a radical polymerizable monomer (b) containing no acidic group, a chemical polymerization initiator (f), and a filler (h), and the second agent comprises a radical polymerizable monomer (b) containing no acidic group, a polymerization accelerator (c), a photopolymerization initiator (g), and a filler (h). Another preferred embodiment (X-2) is, for example, a dental adhesive material kit of embodiment (X-1) in which the first agent comprises a photopolymerization accelerator. Another preferred embodiment (X-3) is, for example, a dental adhesive material kit of embodiment (X-1) or (X-2) in which the first agent comprises a ultraviolet absorber. Another preferred embodiment (X-4) is, for example, a dental adhesive material kit of any of embodiments (X-1) to (X-3) in which the first agent and/or the second agent comprise a polymerization inhibitor. Another preferred embodiment (X-5) is, for example, a dental adhesive material kit of any of the preferred embodiments (X-1) to (X-4) in which the dental aqueous adhesive composition (A) comprises a radical polymerizable monomer (a) containing an acidic group, a radical polymerizable monomer (b-1) containing no amino group and no acidic group, a polymerization accelerator (c), and water (d). Another preferred embodiment (X-6) is, for example, a dental adhesive material kit of embodiment (X-5) in which the dental aqueous adhesive composition (A) comprises a radical polymerizable monomer (b-2) containing an amino group but no acidic group. In all of the embodiments (X-1) to (X-6) described above, the amount of each component may be varied as appropriate, and changes such as addition and deletion may be made for any desired components following the descriptions above. In all of the embodiments above, the compositions and the properties (e.g., tensile bond strength, flexural strength) of the dental adhesive material kits may have values different from the values specified above, and the values may be combined as appropriate.

A dental adhesive material kit of the present invention has desirable adhesive properties for tooth structure, and, while ensuring appropriate strength, enables easy removal of a marginal excess cement in a semi-cured state created by temporarily applying light to excess portions of cement with a photoirradiator in bonding a crown restoration to tooth structure. This makes a dental adhesive material kit of the present invention suitable for use in dentistry. When using a dental adhesive material kit of the present invention in dentistry, the dental adhesive material kit may comprise the dental aqueous adhesive composition (A) as a dental primer, and the dental curable composition (B) as, for example, a dental bonding material, a dental composite resin, or a dental resin cement. Preferably a dental adhesive material kit of the present invention is a dental cement kit. In a more preferred form, a dental adhesive material kit of the present invention is a dental cement kit that comprises the dental aqueous adhesive composition (A) as a dental primer, and the dental curable composition (B) as a dental resin cement.

EXAMPLES

The following describes the present invention by way of Examples and Comparative Examples. However, the present invention is in no way limited by the following descriptions. The following abbreviations are used in Examples and Comparative Examples.
Radical Polymerizable Monomer (a) Containing an Acidic Group
 MDP: 10-Methacryloyloxydecyl dihydrogen phosphate
Radical Polymerizable Monomer (b-1) Containing No Amino Group and No Acidic Group
 HEMA: 2-Hydroxyethyl methacrylate
 #801: 1,2-Bis(3-methacryloyloxy-2-hydroxypropoxy)ethane
 BisGMA: 2,2-Bis[4-(3-methacryloyloxy-2-hydroxypropoxy)phenyl]propane
 D2.6E: 2,2-Bis(4-methacryloyloxypolyethoxyphenyl)propane (average number of moles of ethoxy groups added: 2.6)
 3G: Triethylene glycol dimethacrylate
Radical Polymerizable Monomer (b-2) Containing an Amino Group but No Acidic Group
 DMAEMA: Dimethylaminoethyl methacrylate (pH adjuster)
Thiourea Compound (c-2)
 DMETU: 4,4-Dimethylethylene thiourea
Vanadium Compound (c-3-1)
 VOAA: Vanadyl acetylacetonate
 BMOV: Bis(maltolato)oxovanadium(IV)
Copper Compound (c-3-2)
 $Cu(OAc)_2$: Copper(II) acetate
 $CuAA_2$: copper(II) acetylacetonate
Chemical Polymerization Initiator (f)
 THP: 1,1,3,3-Tetramethylbutyl hydroperoxide
Polymerization Inhibitor
 BHT: 3,5-Di-t-butyl-4-hydroxytoluene
Ultraviolet Absorber
 TN326: Tinuvin 326 (manufactured by BASF Japan Ltd.)
Photopolymerization Initiator (g)
 CQ: Camphorquinone
Photopolymerization Accelerator
 JJA: Ethyl 4-(N,N-dimethylamino)benzoate
Filler (h)
 8235: A silane-treated barium glass powder manufactured by Schott; average particle diameter: 2 μm, concentration of silane treatment: 1.4%
 G018-117: A silane-treated barium fluoroaluminosilicate glass powder manufactured by Schott; average particle diameter: 2 μm, concentration of silane treatment: 1.4%
 Ar380: Afine silica particle AEROSIL® 380 manufactured by Nippon Aerosil Co., Ltd.; average particle diameter: 7 nm Examples 1 to 6 and Comparative Examples 1 to 3

Dental aqueous adhesive compositions (A) and dental curable compositions (B) were prepared for Examples and Comparative Examples in the manner described below, and the properties of these compositions were evaluated. The results are presented in Table 2.
Preparation of Dental Aqueous Adhesive Composition (A)
 The raw materials were mixed under ordinary temperature (25° C.) in the mass ratio shown in Table 2 to prepare a primer as dental aqueous adhesive composition (A). The primer properties were then evaluated according to the methods described below.
Preparation of Dental Curable Composition (B)
 The raw materials were mixed under ordinary temperature (25° C.) in the mass ratios shown in Table 1 to prepare a first monomer composition and a second monomer composition. At ordinary temperature, each monomer composition was mixed with fillers in the mass ratios shown in Table 2 to prepare a first paste and a second paste. For only the second paste, 15 g of paste was transferred to a resin container designed for Clearfil® FII (manufactured by Kuraray Noritake Dental Inc.). The second paste was then left to stand in a 60° C. thermostatic chamber for 24 hours after placing a cap on the container, and was brought back to ordinary temperature (25° C.). After preparation, the first and second pastes were separately charged into paste containers (an automix syringe designed for Clearfil® Esthetic Cement manufactured by Kuraray Noritake Dental Inc.). For evaluations using a dental curable composition (B) prepared by mixing the first and second pastes, the first paste and second paste were kneaded in a 1:1 volume ratio using a mixing tip (Clearfil® Esthetic Cement Mixing Tip, manufactured by Kuraray Noritake Dental Inc.) attached to the tip of the paste container, and the resulting dental curable composition (B) was used for evaluations, as will be described later.
Method of Evaluation of Tensile Bond Strength to Bovine Dentin
 The labial surfaces of bovine mandibular incisors were ground with #80 silicon carbide paper (manufactured by Nihon Kenshi Co., Ltd.) under running water to obtain samples with an exposed flat dentin surface. The samples were then polished with #1000 silicon carbide paper (manufactured by Nihon Kenshi Co., Ltd.) under running water. For each sample, the polished surface was dried by removing water by air-blowing. After drying, an about 150 µm-thick adhesive tape having a 3 mm circular hole was attached to the dried smooth dentin surface to define a bonding area.

The dental aqueous adhesive composition (A) prepared was then applied to the circular hole with a brush. After being left to stand for 20 seconds, the surface was dried by blowing air until the applied dental aqueous adhesive composition (A) was no longer flowable. Thereafter, a dental curable composition (B) prepared by kneading the first paste and second paste in a 1:1 volume ratio using the afore-mentioned mixing tip was placed on the surface of dental aqueous adhesive composition (A). After placing a release film (manufactured by Kuraray Co., Ltd. under the trade name Eval®), the dental curable composition (B) was cured by being left to stand at ordinary temperature for 1 hour. A cylindrical stainless steel rod (measuring 7 mm in diameter and 2.5 cm in length) was then bonded at its one end face (circular end face) to the cured surface, using a dental resin cement (Panavia® 21, manufactured by Kuraray Noritake Dental Inc.). The bonded sample was left to stand for 30 minutes, and was immersed in distilled water after removing the excess dental resin cement from around the cylindrical stainless steel rod. The sample immersed in distilled water was then left to stand in a thermostatic chamber for 24 hours at the maintained temperature of 37° C. to prepare a sample for adhesion testing. Here, a total of 10 adhesion test samples were prepared.

Five of the adhesion test samples were measured for tensile bond strength using a universal testing machine (Shimadzu Corporation) with the crosshead speed set to 2 mm/min, and the mean value was calculated as an initial tensile bond strength.

For the remaining five adhesion test samples, tensile bond strength was measured after placing the sample under a thermal cycle (TC) by alternately immersing the sample in a 4° C. water tank and a 60° C. water tank for a total of 10,000 times, one minute each. The tensile bond strength after this thermal cycle was then evaluated as bond durability.

Method of Evaluation of Flexural Strength and Elastic Modulus of Cured Paste

A polyester film was laid over a glass slide, and a stainless-steel mold, measuring 2 mm in length, 25 mm in width, and 2 mm in depth, was mounted on the film. A dental curable composition (B) prepared by kneading the first paste and second paste in a 1:1 volume ratio using a mixing tip was then filled into the mold. After laying another polyester film over the composition filling the mold, another glass slide was placed on this polyester film. The glass slides were then pressed against the surfaces of the compositing filling the mold, via the polyester films, and the glass slides were secured with 25 mm-wide binder clips. With the binder clips securing the glass slides, the sample was polymerized and cured by being left to stand in a 37° C. thermostatic chamber for 1 hour, and the cured product of dental curable composition (B) was removed from the mold after taking the sample out of the thermostatic chamber. For storage, the cured product was immersed in 37° C. distilled water for 24 hours, and a flexure test was conducted using this specimen. The specimen was measured for flexural strength and flexural modulus in a three-point flexural test carried out with a span length of 20 mm and a crosshead speed of 1 mm/min, using a universal testing machine (manufactured by Shimadzu Corporation). The mean values of flexural strength and flexural modulus from five specimens were determined as the flexural strength and flexural modulus of the cured paste.

Method of Evaluation of Removability of Excess Cement by Temporary Exposure to Light The labial surfaces of bovine mandibular incisors were ground with #80 silicon carbide paper (manufactured by Nihon Kenshi Co., Ltd.) under running water to obtain samples with an exposed flat dentin surface. The samples were then polished with #1000 silicon carbide paper (manufactured by Nihon Kenshi Co., Ltd.) under running water. The bovine tooth samples were used for testing after being left to stand in an open chamber for 2 hours with the temperature set to 35° C.

After being left to stand in the open chamber, the bovine tooth sample was dried by blowing air against the water on sample surface. With the flat smooth surface facing up, the sample was immobilized on a glass slide using a Utility Wax (manufactured by GC). The glass slide with the bovine tooth sample was placed on the work surface of the open chamber, and the sample position was adjusted to make the flat smooth surface of sample parallel to the work surface. Thereafter, the dental aqueous adhesive composition (A) prepared was applied to the flat smooth surface with a brush, and, after being left to stand for 20 seconds, the surface was dried by blowing air until the applied dental aqueous adhesive composition (A) was no longer flowable.

A dental curable composition (B) prepared by kneading the first paste and second paste in a 1:1 volume ratio using the afore-mentioned mixing tip was placed on one end face (circular end face) of a cylindrical stainless steel rod (measuring 7 mm in diameter and 2.5 cm in length; hereinafter, referred to as "SUS chip"). The SUS chip was then gently placed on the bovine tooth sample in such an orientation that the surface with the applied composition contacted the flat smooth surface of the bovine tooth sample. The test sample prepared in the fashion had the dental curable composition (B) extruding out from around the SUS chip. (This portion of dental curable composition (B) corresponds to excess cement.)

The test sample prepared was brought back into the thermostatic chamber held at 37° C., and an excess cement removability test was conducted (n=3). From a distance of about 1 cm from the test sample, the excess cement was irradiated with light using a dental LED photoirradiator for polymerization (PenCure 2000, manufactured by J. Morita Corp.) in standard mode. Light was applied for 10 seconds in one circle, 1 minute after the excess cement had extruded from the applied dental curable composition (B) under the SUS chip in the test sample. For each test sample exposed to light for 10 seconds after 1 minute, the excess cement was immediately removed by applying a dental explorer to the interface between the excess cement and the SUS chip. Removability of excess cement by temporary exposure to light was evaluated using the following criteria. Specifically, samples had an A score when all three samples satisfied the criterion A, and a C score when any of the samples fell into category C.

Evaluation Criteria for Removability of Excess Cement

A: Excess cement is easily removable in one piece

B: Strong adhesion to tooth structure, but excess cement is removable in multiple pieces C: Excess cement is very hard and not easily removable, or removal of excess cement is difficult because of many unpolymerized portions being present in excess cement Method of Measurement of Contactual Polymerization Start Time t1 and Polymerization Start Time t2

A diamond micro ATR unit (a single-reflection horizontal-type ATR Smart Orbit) was installed in a FT-IR spectrometer (Fourier Transformation Infrared Spectrometer Nicolet 6700, manufactured by Thermo Fisher Scientific). Measurements were made across a 4,000 cm$^{-1}$ to 650 cm$^{-1}$ band in a single scan.

Measurement for t2

Figure 2A:
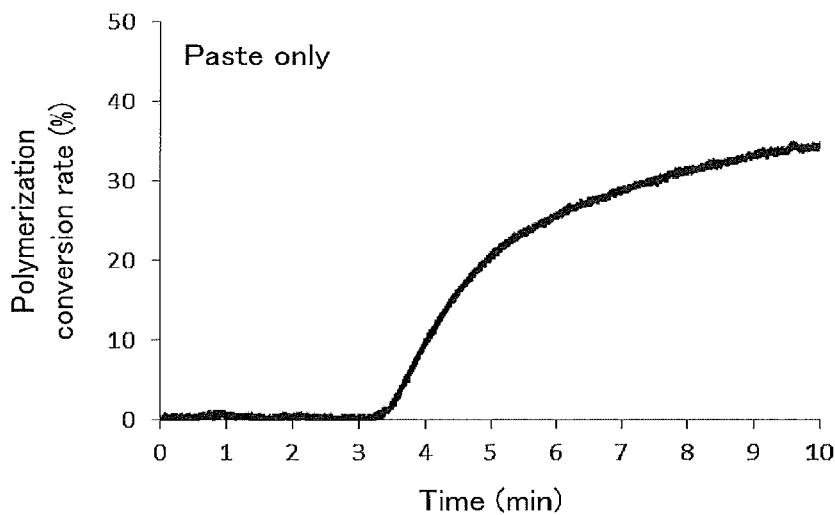
FIG. 2A is a diagram representing the polymerization behavior of the dental adhesive material kit of Example 1 of when a dental curable composition (B) is used alone.
Figure 2B:
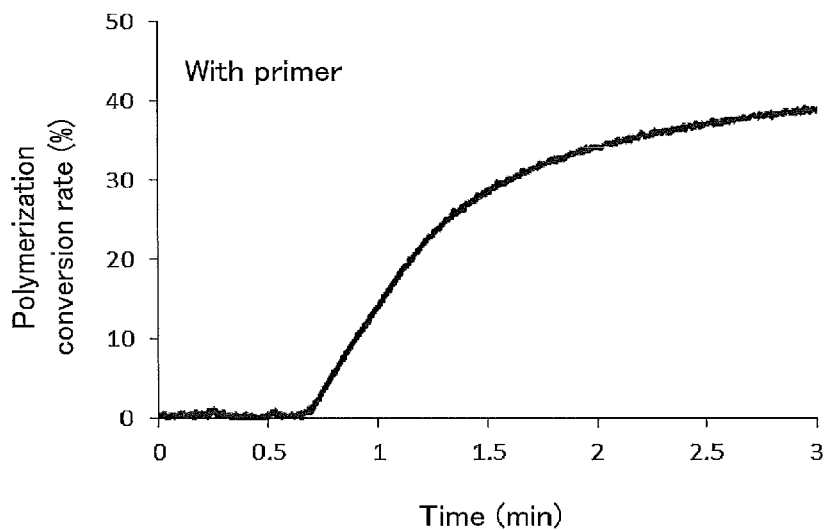
FIG. 2B is a diagram representing the polymerization behavior of the dental adhesive material kit of Example 1 of when a dental aqueous adhesive composition (A) and a dental curable composition (B) are in contact with each other.
Figure 3A:
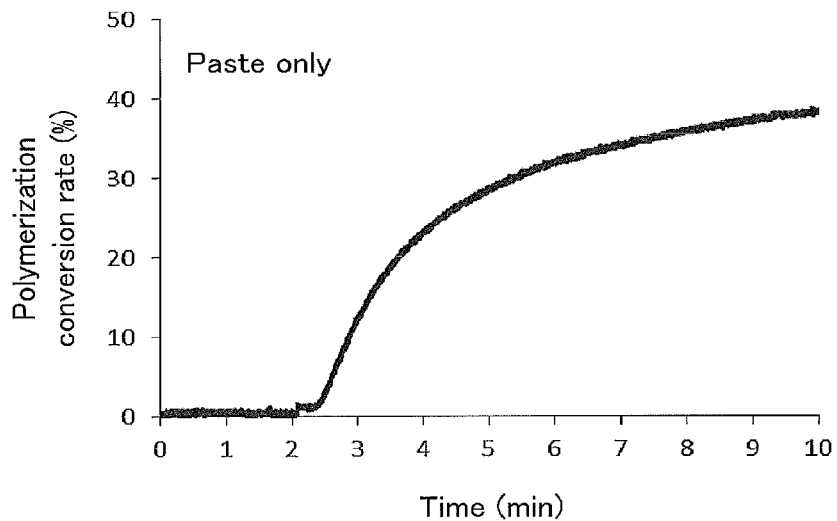
FIG. 3A is a diagram representing the polymerization behavior of the dental adhesive material kit of Example 2 of when a dental curable composition (B) is used alone.
Figure 3B:
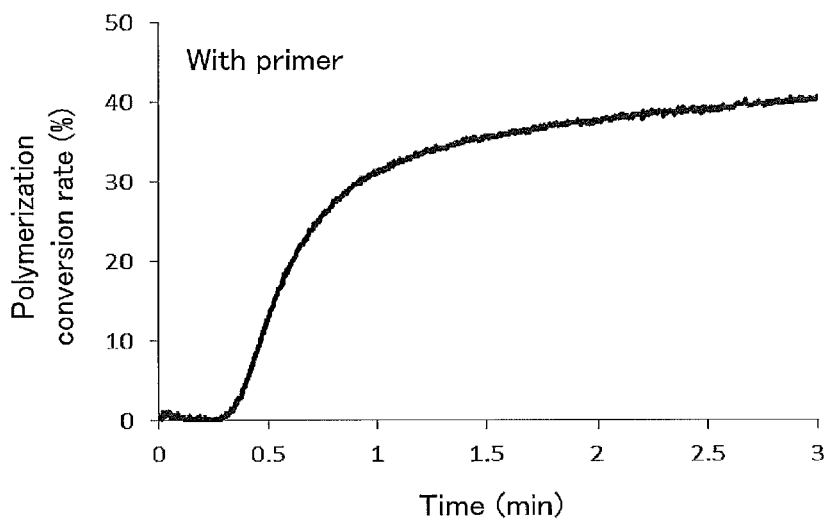
FIG. 3B is a diagram representing the polymerization behavior of the dental adhesive material kit of Example 2 of when a dental aqueous adhesive composition (A) and a dental curable composition (B) are in contact with each other.
Figure 4A:
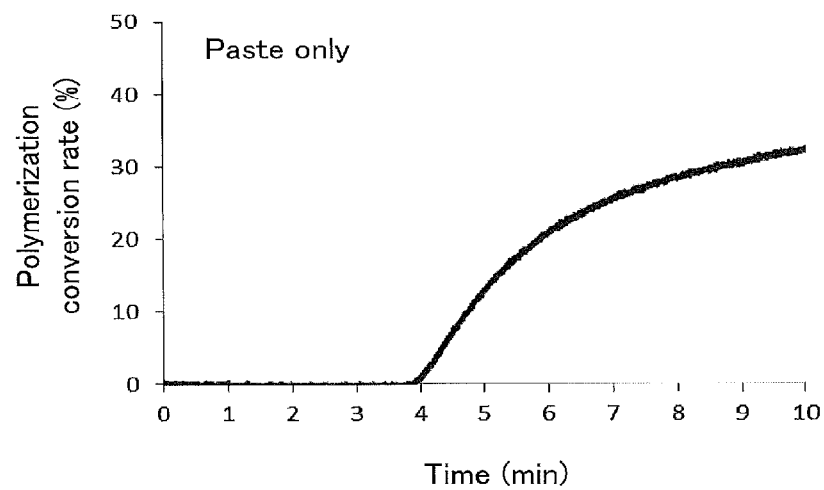
FIG. 4A is a diagram representing the polymerization behavior of the dental adhesive material kit of Comparative Example 1 of when a dental curable composition (B) is used alone.
Figure 4B:
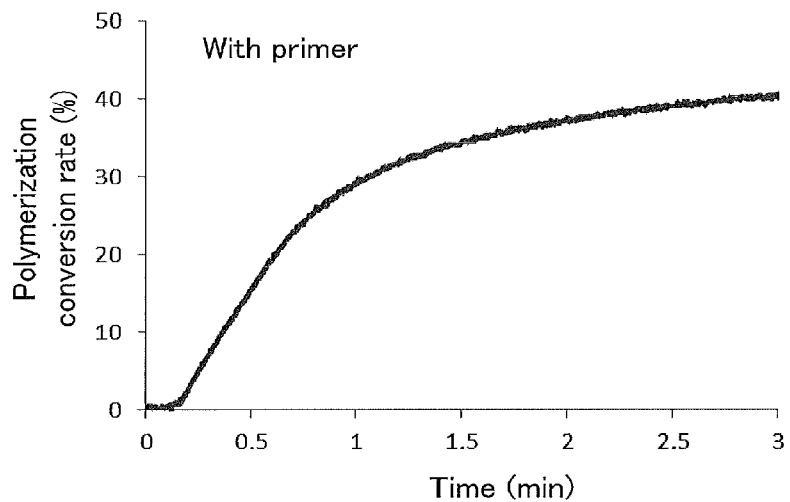
FIG. 4B is a diagram representing the polymerization behavior of the dental adhesive material kit of Comparative Example 1 of when a dental aqueous adhesive composition (A) and a dental curable composition (B) are in contact with each other.
Figure 5A:
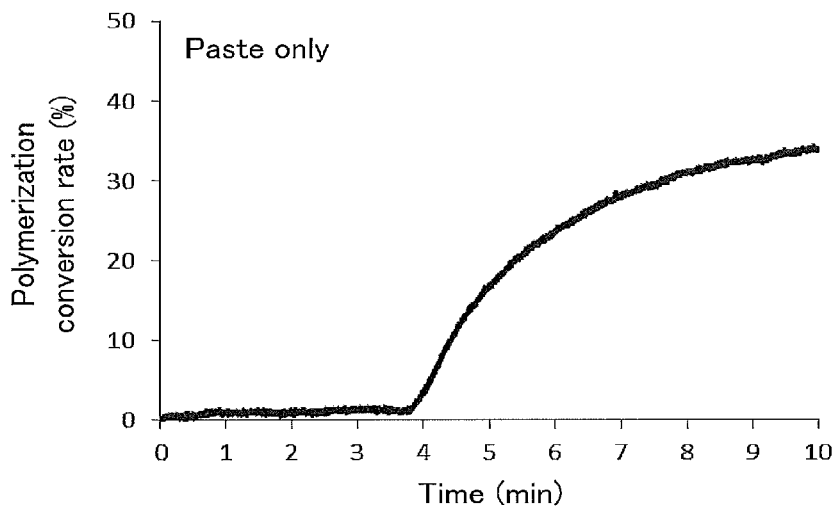
FIG. 5A is a diagram representing the polymerization behavior of the dental adhesive material kit of Comparative Example 2 of when a dental curable composition (B) is used alone.
Figure 5B:
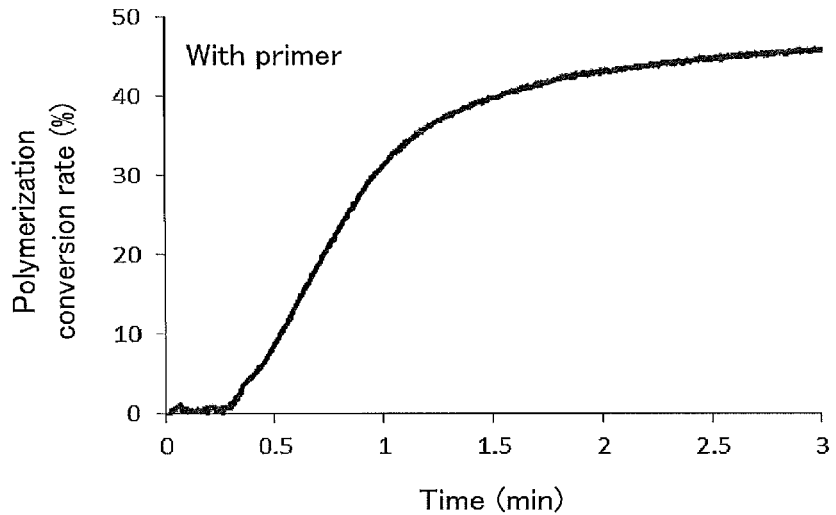
FIG. 5B is a diagram representing the polymerization behavior of the dental adhesive material kit of Comparative Example 2 of when a dental aqueous adhesive composition (A) and a dental curable composition (B) are in contact with each other.

A dental curable composition (B) prepared by kneading the first paste and second paste in a 1:1 volume ratio using the afore-mentioned mixing tip was placed on the stage of the diamond micro ATR unit set to 32° C. Real time IR spectroscopy was then performed for the spectral measurement of dental curable composition (B) at each time point. The real time IR measurement was started upon kneading the first and second pastes, as shown in, for example, FIG. 2A and FIG. 3A.

Measurement for t1 and $V_{max}$

Separately, a dental aqueous adhesive composition (A) prepared in the manner described above was applied to the stage of the diamond micro ATR unit set to 32° C., using a brush. The surface was dried by blowing air until the applied dental aqueous adhesive composition (A) was no longer flowable. Thereafter, a dental curable composition (B) prepared by kneading the first paste and second paste in a 1:1 volume ratio using the afore-mentioned mixing tip was placed on the dental aqueous adhesive composition (A). Real time IR spectroscopy was then performed for the spectral measurement of dental curable composition (B) at each time point with dental aqueous adhesive composition (A). The real time IR measurement was started upon contacting the dental curable composition (B) with the dental aqueous adhesive composition (A).

The spectrum was analyzed as follows. With a baseline set between 1,659 cm$^{-1}$ and 1,550 cm$^{-1}$, peaks a1 and a2 attributed to the carbonyl bond before and after polymerization (C=O, 1,700 cm$^{-1}$), unaffected by polymerization from the baseline, were chosen as references. The area ratios of b1 and b2 with respect to these references (b1/a1, b2/a2) were then used to determine the percentage of remaining double bonds and a polymerization conversion rate c (%), where b1 and b2 are peaks attributed to the double bond before and after polymerization (C=C, 1,600 cm$^{-1}$). These were used for the calculation of t1, t2, and $V_{max}$, as follows (see FIG. 1).

Relative ratio of double bonds before polymerization: b1/a1
Relative ratio of double bonds after polymerization: b2/a2

$$\text{Percentage of remaining double bonds} = (b2 \times a1/b1 \times a2) \times 100$$

$$\text{Polymerization conversion rate } c\ (\%) = \{1 - (b2 \times a1)/(b1 \times a2)\} \times 100$$

$$\text{Average polymerization rate } V\ (\%/\min) = (cy - cx)/(ty - tx)$$

cx, cy: Polymerization conversion rates at time tx and time ty (min) (ty>tx)

$$cx = \{1 - (bx \times a1)/(b1 \times ax)\} \times 100$$

$$cy = \{1 - (by \times a1)/(b1 \times ay)\} \times 100$$

ax, ay: Areas of peaks attributed to the carbonyl bond at time tx and time ty (ty>tx)

bx, by: Areas of peaks attributed to the double bond at time tx and time ty (ty>tx)

The maximum contactual polymerization rate $V_{max}$ (%/min) of dental aqueous adhesive composition (A) and dental curable composition (B) is the maximum value of average polymerization rate V.

The polymerization start time t2 (min) of dental curable composition (B) is the minimum value of tx satisfying an average polymerization rate V≥5 (%/min) when the first and second pastes of dental curable composition (B) are kneaded.

The contactual polymerization start time t1 (min) of dental aqueous adhesive composition (A) and dental curable composition (B) is the minimum value of tx satisfying an average polymerization rate V≥5 (%/min) when the dental curable composition (B) obtained by kneading the first paste and second paste is in contact with the dental aqueous adhesive composition (A).

TABLE 1

| Components (parts by mass) | | Ex. 1 | Ex. 2 | Ex. 3 | Ex. 4 | Ex. 5 | Ex. 6 | Com. Ex. 1 | Com. Ex. 2 | Com. Ex. 3 |
|---|---|---|---|---|---|---|---|---|---|---|
| First monomer composition | | | | | | | | | | |
| Radical polymerizable monomer (b-1) containing no amino group and no acidic group | BisGMA | 36 | 36 | 36 | 36 | 36 | 36 | 36 | 36 | 36 |
| | D2.6E | 35 | 35 | 35 | 35 | 35 | 35 | 35 | 35 | 35 |
| | 3G | 17 | 17 | 17 | 17 | 17 | 17 | 17 | 17 | 17 |
| | #801 | 10 | 10 | 10 | 10 | 10 | 10 | 10 | 10 | 10 |
| Chemical polymerization initiator (f) | THP | 4 | 4 | 4 | 4 | 4 | 4 | 4 | 4 | 4 |
| Photopolymerization accelerator | JJA | 0.25 | 0.25 | 0.25 | 0.25 | 0.25 | 0.25 | 0.25 | 0.25 | 0.25 |
| UV absorber | TN326 | 0.225 | 0.225 | 0.225 | 0.225 | 0.225 | 0.225 | 0.225 | 0.225 | 0.225 |
| Polymerization inhibitor | BHT | 0.05 | 0.05 | 0.05 | 0.05 | 0.05 | 0.05 | 0.05 | 0.05 | 0.05 |
| Second monomer composition | | | | | | | | | | |
| Radical polymerizable monomer (b-1) containing no amino group and no acidic group | BisGMA | 15 | 15 | 15 | 15 | 15 | 15 | 15 | 15 | 15 |
| | D2.6E | 70 | 70 | 70 | 70 | 70 | 70 | 70 | 70 | 70 |
| | #801 | 15 | 15 | 15 | 15 | 15 | 15 | 15 | 15 | 15 |
| Polymerization accelerator (c) | DMETU | 6.0 | 6.0 | 6.0 | 6.0 | 6.0 | 6.0 | 6.0 | 6.0 | 6.0 |
| | VOAA | 0.04 | 0.08 | 0.04 | | 0.02 | | 0.1 | 0.08 | 0.08 |
| | BMOV | | | | | | 0.04 | | | |

TABLE 1-continued

| Components (parts by mass) | | Ex. 1 | Ex. 2 | Ex. 3 | Ex. 4 | Ex. 5 | Ex. 6 | Com. Ex. 1 | Com. Ex. 2 | Com. Ex. 3 |
|---|---|---|---|---|---|---|---|---|---|---|
| | Cu(OAc)$_2$ | 0.002 | 0.005 | | 0.005 | 0.005 | 0.002 | | 0.001 | |
| | CuAA$_2$ | | | 0.002 | | | | | | 0.0025 |
| Photopolymerization initiator (g) | CQ | 0.2 | 0.2 | 0.2 | 0.2 | 0.2 | 0.2 | 0.2 | 0.2 | 0.2 |
| Polymerization inhibitor | BHT | 0.05 | 0.05 | 0.05 | 0.05 | 0.05 | 0.05 | 0.05 | 0.05 | 0.05 |

TABLE 2

| Components (parts by mass) | | Ex. 1 | Ex. 2 | Ex. 3 | Ex. 4 | Ex. 5 | Ex. 6 | Com. Ex. 1 | Com. Ex. 2 | Com. Ex. 3 |
|---|---|---|---|---|---|---|---|---|---|---|
| Primer | | | | | | | | | | |
| Radical polymerizable monomer (a) containing an acidic group | MDP | 15 | 15 | 15 | 15 | 15 | 15 | 15 | 15 | 15 |
| Radical polymerizable monomer (b-1) containing no amino group and no acidic group | HEMA | 15 | 15 | 15 | 15 | 15 | 15 | 15 | 15 | 15 |
| | #801 | 35 | 35 | 35 | 35 | 35 | 35 | 35 | 35 | 35 |
| Radical polymerizable monomer (b-2) containing an amino group but no acidic group | DMAEMA | 2.7 | 2.7 | 2.7 | 2.7 | 2.7 | 2.7 | 2.7 | 2.7 | 2.7 |
| Polymerization accelerator (c) | VOAA | 0.5 | 0.5 | 0.5 | 0.5 | 0.5 | 0.5 | 0.5 | 0.5 | 0.5 |
| Water (d) | H$_2$O | 32 | 32 | 32 | 32 | 32 | 32 | 32 | 32 | 32 |
| Polymerization inhibitor | BHT | 2 | 2 | 2 | 2 | 2 | 2 | 2 | 2 | 2 |
| First paste | | | | | | | | | | |
| First monomer composition | | 38 | 38 | 38 | 38 | 38 | 38 | 38 | 38 | 38 |
| Filler (h) | 8235 | 51 | 51 | 51 | 51 | 51 | 51 | 51 | 51 | 51 |
| | G018-117 | 10 | 10 | 10 | 10 | 10 | 10 | 10 | 10 | 10 |
| | Ar380 | 1 | 1 | 1 | 1 | 1 | 1 | 1 | 1 | 1 |
| Second paste | | | | | | | | | | |
| Second monomer composition | | 42 | 42 | 42 | 42 | 42 | 42 | 42 | 42 | 42 |
| Filler (h) | 8235 | 57 | 57 | 57 | 57 | 57 | 57 | 57 | 57 | 57 |
| | Ar380 | 1 | 1 | 1 | 1 | 1 | 1 | 1 | 1 | 1 |
| Properties | | | | | | | | | | |
| Tensile bond strength to dentin After 24 hours at 37° C. (MPa) | | 25.6 | 24.3 | 20.1 | 18.6 | 20.5 | 21.4 | 20.4 | 21.6 | 17.8 |
| Tensile bond strength to dentin After TC, 10,000 times (MPa) | | 23.1 | 22.3 | 20.6 | 13.2 | 14.5 | 20.5 | 21.5 | 22.1 | 12.6 |
| Flexural strength of cured paste (MPa) | | 110.2 | 123.2 | 117.4 | 109.3 | 113.5 | 105.4 | 115.4 | 112.1 | 106.9 |
| Elastic modulus of cured paste (GPa) | | 5.0 | 5.1 | 5.0 | 4.5 | 4.8 | 4.9 | 5.2 | 4.8 | 4.4 |
| Removability of excess cement by temporary exposure to light | | A | A | A | A | A | A | C | B | B |
| Polymerization start time t2 of dental curable composition (B) (min) | | 3.54 | 2.35 | 3.45 | 2.90 | 2.64 | 3.64 | 4.00 | 3.84 | 3.96 |
| Contactual polymerization start time t1 of dental aqueous adhesive composition (A) and dental curable composition (B) (min) | | 0.64 | 0.34 | 0.54 | 0.45 | 0.46 | 0.70 | 020 | 0.30 | 0.81 |
| Difference of polymerization start time t2-t1 (min) | | 2.90 | 2.01 | 2.91 | 2.45 | 2.18 | 0.94 | 3.80 | 3.54 | 3.15 |
| Maximum contactual polymerization rate V$_{max}$ of dental aqueous adhesive composition (A) and dental curable composition (B) (%/min) | | 44.3 | 79.6 | 47.3 | 32.7 | 37.4 | 42.1 | 45.4 | 49.7 | 28.7 |

As can be seen from the results shown in Table 2, the dental adhesive material kits of the present invention have more desirable initial adhesive properties and higher bond durability for dentin than Comparative Examples. It can also be seen that the dental adhesive material kits of the present invention enable easy removal of excess cement by photoirradiation.

INDUSTRIAL APPLICABILITY

A dental adhesive material kit of the present invention has desirable adhesive properties for tooth structure, and, while ensuring appropriate strength, enables easy removal of excess cement in a semi-cured state created by temporarily applying light to excess portions of cement with a photoirradiator. This makes a dental adhesive material kit of the present invention particularly suitable as a dental cement kit.

The invention claimed is:

1. A dental adhesive material kit, comprising:
   (A) a dental aqueous adhesive composition; and
   (B) a dental curable composition,
   wherein the dental adhesive material kit satisfies inequality (I):

$$0 \leq t2-t1 \leq 3.0 \qquad (I),$$

wherein
   t1 (min) is a contactual polymerization start time of the dental aqueous adhesive composition (A) and the dental curable composition (B), and
   t2 (min) is a polymerization start time of the dental curable composition (B),
   wherein the dental aqueous adhesive composition (A) comprises (a) a radical polymerizable monomer comprising an acidic group; (b-1) a first radical polymerizable monomer comprising no amino group and no acidic group; (c-1) a first polymerization accelerator; and (d) water,
   wherein the dental curable composition (B) comprises (b) a second radical polymerizable monomer comprising no acidic group; (c-2) a second polymerization accelerator; (f) a chemical polymerization initiator;initiator, (g) a photopolymerization initiator; initiator, and (h) a filler,
   wherein the second polymerization accelerator (c-2) in the dental curable composition (B) comprises a first period 4 transition metal compound, and
   wherein the first period 4 transition metal compound comprises a vanadium compound in a range of from 0.01 to 0.04 parts by mass and a copper compound in a range of from 0.001 to 0.0025 parts by mass, relative to 100 parts by mass of the radical polymerizable monomer (b) in the dental curable composition (B).

2. The kit of claim 1, wherein the dental aqueous adhesive composition (A) and the dental curable composition (B) have a maximum contactual polymerization rate $V_{max}$ of 40%/min or more.

3. The kit of claim 1, wherein the first polymerization accelerator (c-1) in the dental aqueous adhesive composition (A) also comprises the first period 4 transition metal compound.

4. The kit of claim 1, wherein t1 (min) is in a range of from more than 0.1 to 3.0 minutes.

5. The kit of claim 1, wherein t2 (min) is in a range of from 2.35 to less than 4.0 minutes.

6. The kit of claim 1, wherein the chemical polymerization initiator (f) in the dental curable composition (B) comprises a hydroperoxide.

7. The kit of claim 1, wherein the first polymerization accelerator (c-1) in the dental aqueous adhesive composition (A) comprises the first period 4 transition metal compound.

8. The kit of claim 1, wherein the second polymerization accelerator (c-2) in the dental curable composition (B) comprises a thiourea compound.

9. The kit of claim 1, wherein the dental curable composition (B) is a two-pack type.

10. The kit of claim 1, which is a dental cement kit.

11. The kit of claim 1, wherein the second polymerization accelerator (c-2) in the dental curable composition (B) further comprises a second period 4 transition metal compound.

12. The kit of claim 1, wherein the radical polymerizable monomer (a) comprises a (meth)acrylic polymerizable monomer comprising a phosphoric acid group.

13. The kit of claim 1, wherein the radical polymerizable monomer (a) comprises 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, 2-(meth)acryloyloxyethylphenyl hydrogen phosphate, 2-(meth)acryloyloxyethyl-2-bromoethyl hydrogen phosphate, 2-methacryloyloxyethyl-(4-methoxyphenyl) hydrogen phosphate, and/or 2-methacryloyloxypropyl-(4-methoxyphenyl) hydrogen phosphate, optionally as an acid chloride or salt.

14. The kit of claim 1, wherein the radical polymerizable monomer (a) comprises bis [2-(meth)acryloyloxyethyl] hydrogen phosphate, bis [4-(meth)acryloyloxybutyl] hydrogen phosphate, bis [6-(meth)acryloyloxyhexyl] hydrogen phosphate, bis [8-(meth)acryloyloxyoctyl] hydrogen phosphate, bis [9-(meth)acryloyloxynonyl] hydrogen phosphate, bis [10-(meth)acryloyloxydecyl] hydrogen phosphate, and/or 1,3-di(meth)acryloyloxypropyl dihydrogen phosphate, optionally as an acid chloride or salt.

15. The kit of claim 1, wherein the radical polymerizable monomer (a) comprises bis [2-(meth)acryloyloxyethyl] pyrophosphate, bis [4-(meth)acryloyloxybutyl] pyrophosphate, bis [6-(meth)acryloyloxyhexyl] pyrophosphate, bis [8-(meth)acryloyloxyoctyl] pyrophosphate, bis [10-(meth)acryloyloxydecyl] pyrophosphate, 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, 20-(meth)acryloyloxyeicosyl dihydrogen thiophosphate, 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexylphosphonoacetate, and/or 10-(meth)acryloyloxydecylphosphonoacetate, optionally as an acid chloride or salt.

16. The kit of claim 1, wherein the first radical polymerizable monomer (b-1) comprises a (meth)acrylic acid ester and/or a (meth)acrylamide.

17. The kit of claim 1, wherein the first polymerization accelerator (c-1) comprises a borate compound.

18. The kit of claim 1, wherein the radical polymerizable monomer (a) comprises bis [2-(meth)acryloyloxyethyl] hydrogen phosphate, optionally as a salt.

19. The kit of claim 1, wherein the radical polymerizable monomer (a) comprises bis [4-(meth)acryloyloxybutyl] hydrogen phosphate, optionally as a salt.

20. The kit of claim 1, wherein the radical polymerizable monomer (a) comprises bis [6-(meth)acryloyloxyhexyl] hydrogen phosphate, optionally as a salt.

* * * * *